(12) United States Patent
Curtin et al.

(10) Patent No.: US 12,329,405 B2
(45) Date of Patent: *Jun. 17, 2025

(54) CUTTING ASSEMBLY FOR SURGICAL INSTRUMENT WITH CLOG-REDUCING TIP

(71) Applicant: Stryker European Operations Holdings LLC, Portage, MI (US)

(72) Inventors: Damian Michael Curtin, Kerry (IE); Patrick Eoin Cushen, Cork (IE)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/227,405

(22) Filed: Jul. 28, 2023

(65) Prior Publication Data

US 2023/0363783 A1 Nov. 16, 2023

Related U.S. Application Data

(63) Continuation of application No. 17/331,795, filed on May 27, 2021, now Pat. No. 11,766,274, which is a
(Continued)

(51) Int. Cl.
*A61B 17/32* (2006.01)
*A61B 17/00* (2006.01)

(52) U.S. Cl.
CPC ..... *A61B 17/32002* (2013.01); *A61B 2017/0046* (2013.01); *A61B 2017/320008* (2013.01);
(Continued)

(58) Field of Classification Search
CPC .............. A61B 17/32002; A61B 17/32; A61B 17/320016; A61B 17/320068;
(Continued)

(56) References Cited

U.S. PATENT DOCUMENTS

| 4,850,354 A | 7/1989 | McGurk-Burleson et al. |
| 5,286,253 A | 2/1994 | Fucci |

(Continued)

FOREIGN PATENT DOCUMENTS

| CN | 1758880 A | 4/2006 |
| CN | 102961173 A | 3/2013 |

(Continued)

OTHER PUBLICATIONS

English language abstract for CN 102961173 A extracted from espacenet.com database on Mar. 25, 2024, 2 pages.
(Continued)

*Primary Examiner* — Katherine M Shi
*Assistant Examiner* — Mohammed S Adam
(74) *Attorney, Agent, or Firm* — Howard & Howard Attorneys PLLC

(57) ABSTRACT

A cutting assembly configured to be removably coupled to a drive assembly of a surgical instrument. An inner tube is coaxially and rotatably disposed within an outer tube and defines a lumen in communication with a cutting window. A projection is disposed within the lumen of the inner tube. The projection may include a distal first portion displaced radially inward relative to an interior surface of the inner tube, and a proximal second portion angled relative to the distal first portion. A distance between a proximal boundary of the cutting window and a nearest point on the projection may be less than a diameter of the lumen. An inner surface of the projection permits cutting action to continue until the material is sufficiently reduced to pass between a proximal boundary of the cutting window and the insert. The projection may be formed by an insert secured within the inner tube.

17 Claims, 14 Drawing Sheets

Related U.S. Application Data continuation of application No. 16/316,500, filed as application No. PCT/US2017/042101 on Jul. 14, 2017, now Pat. No. 11,020,139.

(60) Provisional application No. 62/362,117, filed on Jul. 14, 2016.

(52) U.S. Cl.
CPC .............. *A61B 2017/320024* (2013.01); *A61B 2017/32008* (2013.01); *A61B 2217/005* (2013.01)

(58) Field of Classification Search
CPC .................. A61B 17/22; A61B 17/221; A61B 2017/0046; A61B 2017/320008; A61B 2017/320024; A61B 2017/32008; A61B 2017/320004; A61B 2017/320012; A61B 2017/320028; A61B 2017/320032; A61B 2017/32004; A61B 2017/320044; A61B 2017/320056; A61B 2017/320064; A61B 2017/320072; A61B 2017/320078; A61B 2217/005

See application file for complete search history.

(56) References Cited

U.S. PATENT DOCUMENTS

| | | | |
|---|---|---|---|
| 5,411,514 A | 5/1995 | Fucci et al. | |
| 5,601,583 A | 2/1997 | Donahue et al. | |
| 5,741,287 A | 4/1998 | Alden et al. | |
| 5,755,731 A | 5/1998 | Grinberg | |
| 5,766,199 A | 6/1998 | Heisler et al. | |
| 5,843,106 A | 12/1998 | Heisler | |
| 5,922,003 A | 7/1999 | Anctil et al. | |
| 6,217,598 B1 | 4/2001 | Berman et al. | |
| 6,503,263 B2 | 1/2003 | Adams | |
| RE38,018 E | 3/2003 | Anctil et al. | |
| 6,533,749 B1 | 3/2003 | Mitusina et al. | |
| 6,620,180 B1 | 9/2003 | Bays et al. | |
| 6,656,195 B2 | 12/2003 | Peters et al. | |
| 7,318,831 B2 | 1/2008 | Alvarez et al. | |
| 7,338,495 B2 | 3/2008 | Adams | |
| 7,699,846 B2* | 4/2010 | Ryan ................ | A61B 17/32002 606/177 |
| 7,854,736 B2 | 12/2010 | Ryan | |
| 7,927,361 B2 | 4/2011 | Oliver et al. | |
| 8,088,135 B2 | 1/2012 | Heisler | |
| 8,109,956 B2 | 2/2012 | Shadeck | |
| 8,202,288 B2 | 6/2012 | Adams et al. | |
| 8,277,474 B2 | 10/2012 | Norman et al. | |
| 8,409,235 B2 | 4/2013 | Rubin | |
| 8,435,259 B2 | 5/2013 | Dierck | |
| 8,454,640 B2 | 6/2013 | Johnston et al. | |
| 8,585,724 B2* | 11/2013 | Palmer ................ | A61B 10/0275 606/170 |
| 8,623,266 B2 | 1/2014 | Adams | |
| 8,753,330 B2 | 6/2014 | Drake et al. | |
| 8,758,379 B2 | 6/2014 | Rubin | |
| 8,906,053 B2 | 12/2014 | Oliver et al. | |
| 9,089,344 B2 | 7/2015 | Rubin | |
| 9,308,013 B2 | 4/2016 | Casey et al. | |
| 9,402,645 B2 | 8/2016 | Norman et al. | |
| 9,687,254 B2 | 6/2017 | Shadeck et al. | |
| 9,737,322 B2 | 8/2017 | Oliver et al. | |
| 9,833,258 B2 | 12/2017 | Kusleika | |
| 10,022,144 B2 | 7/2018 | Nguyen et al. | |
| 10,149,698 B2 | 12/2018 | Wulfman et al. | |
| 10,166,013 B2 | 1/2019 | Nguyen et al. | |
| 10,206,706 B2 | 2/2019 | Nguyen | |
| 10,321,929 B2 | 6/2019 | Willhite et al. | |
| 11,806,035 B2 | 11/2023 | Thistle | |
| 11,911,055 B2 | 2/2024 | Gavala et al. | |
| 2004/0059363 A1 | 3/2004 | Alvarez et al. | |
| 2004/0243157 A1* | 12/2004 | Connor ............... | A61M 3/0283 606/159 |
| 2004/0243163 A1 | 12/2004 | Casiano et al. | |
| 2005/0090849 A1 | 4/2005 | Adams | |
| 2008/0188848 A1 | 8/2008 | Deutmeyer et al. | |
| 2008/0208194 A1 | 8/2008 | Bickenbach | |
| 2009/0131816 A1 | 5/2009 | Ritchie et al. | |
| 2010/0211090 A1 | 8/2010 | Berberich | |
| 2011/0196399 A1 | 8/2011 | Robertson et al. | |
| 2012/0101513 A1 | 4/2012 | Shadeck et al. | |
| 2012/0215245 A1 | 8/2012 | Palmer et al. | |
| 2012/0221035 A1 | 8/2012 | Harvey | |
| 2013/0023882 A1 | 1/2013 | Fabro et al. | |
| 2014/0114300 A1 | 4/2014 | Orczy-Timko et al. | |
| 2014/0288560 A1 | 9/2014 | Rubin | |
| 2014/0324086 A1 | 10/2014 | Heisler et al. | |
| 2015/0073364 A1 | 3/2015 | Cheng et al. | |
| 2015/0327880 A1 | 11/2015 | Wasicek et al. | |
| 2015/0335485 A1* | 11/2015 | Rieger ............. | A61B 17/32002 606/171 |
| 2016/0174999 A1 | 6/2016 | Casey et al. | |
| 2016/0206339 A1 | 7/2016 | Akilian et al. | |
| 2019/0216473 A1 | 7/2019 | Edwards | |
| 2019/0223898 A1 | 7/2019 | Curtin et al. | |
| 2019/0298403 A1 | 10/2019 | Willhite et al. | |
| 2021/0282799 A1 | 9/2021 | Curtin et al. | |

FOREIGN PATENT DOCUMENTS

| | | |
|---|---|---|
| CN | 103118720 A | 5/2013 |
| CN | 103252011 A | 8/2013 |
| CN | 203123265 U | 8/2013 |
| CN | 204041829 U | 12/2014 |
| CN | 204072237 U | 1/2015 |
| CN | 204582243 U | 8/2015 |
| CN | 105025823 A | 11/2015 |
| CN | 105636533 A | 6/2016 |
| EP | 2692305 A1 | 2/2014 |
| EP | 3016572 A1 | 5/2016 |
| JP | S61259653 A | 11/1986 |
| JP | H09248307 A | 9/1997 |
| JP | 2005520618 A | 7/2005 |
| JP | 2009543668 A | 12/2009 |
| KR | 20120057643 A | 6/2012 |
| KR | 101486456 B1 | 1/2015 |
| WO | 2007143440 A2 | 12/2007 |
| WO | 2015048270 A1 | 4/2015 |

OTHER PUBLICATIONS

English language abstract for CN 105025823 A extracted from espacenet.com database on Mar. 25, 2024, 2 pages.
English language abstract for CN 105636533 A extracted from espacenet.com database on Mar. 25, 2024, 2 pages.
English language abstract for KR 20120057643 A extracted from espacenet.com database on Jul. 31, 2023, 1 page.
English language abstract and machine-assisted English translation for KR 101486456 B1 extracted from espacenet.com database on Jul. 31, 2023, 13 pages.
English language abstract and machine-assisted English translation for JPH 09-248307 A extracted from espacenet.com database on Sep. 21, 2022, 6 pages.
English language abstract for CN 103252011 A extracted from espacenet.com database on Jun. 14, 2021, 2 pages.
English language abstract for CN 1758880 A extracted from espacenet.com database on Jun. 14, 2021, 2 pages.
English language abstract for JP 2005-520618 A extracted from espacenet.com database on Sep. 21, 2022, 2 pages.
English language abstract for JP 2009-543668 A extracted from espacenet.com database on Sep. 21, 2022, 1 page.
International Search Report for Application No. PCT/US2017/042101 dated Oct. 23, 2017, 3 pages.
Machine-Assisted English translation for JPS 61-259653 extracted from the espacenet.com database on Sep. 16, 2020, 5 pages.
English language abstract and machine-assisted English translation

(56) References Cited

OTHER PUBLICATIONS for CN 203123265 U extracted from espacenet.com database on Aug. 27, 2024, 7 pages.
English language abstract and machine-assisted English translation for CN 204072237 U extracted from espacenet.com database on Aug. 27, 2024, 5 pages.
English language abstract and machine-assisted English translation for CN 204582243 U extracted from espacenet.com database on Aug. 27, 2024, 7 pages.
English language abstract for CN 103118720 A extracted from espacenet.com database on Apr. 29, 2025, 1 page.
English language abstract of CN 204041829 U and machine-assisted English translation for equivalent DE 20 2014 004 809 U1 extracted from espacenet.com database on Apr. 29, 2025, 9 pages.

* cited by examiner

CUTTING ASSEMBLY FOR SURGICAL INSTRUMENT WITH CLOG-REDUCING TIP

CROSS-REFERENCE TO RELATED APPLICATIONS

This is a continuation of copending U.S. patent application Ser. No. 17/331,795, filed May 27, 2021, which is a continuation of U.S. patent application Ser. No. 16/316,500, filed Jan. 9, 2019, now U.S. Pat. No. 11,020,139, which is United States national entry of International Patent Application No. PCT/US2017/042101, filed on Jul. 14, 2017, which claims priority to and all the benefits of U.S. Provisional Patent Application No. 62/362,117, filed on Jul. 14, 2016, the entire contents of each are hereby incorporated by reference.

TECHNICAL FIELD

The present disclosure relates generally to surgical instruments and, more particularly to, a surgical instrument with a clog reducing tip for use on patients.

BACKGROUND

It is known that medical practitioners have found it useful to use surgical instruments to assist in the performance of surgical procedures. A surgical instrument is designed to be applied to a surgical site on the patient. The practitioner is able to position the surgical instrument at the site on the patient at which the instrument is to perform a medical or surgical procedure. Endoscopic surgical procedures are routinely performed in order to accomplish various surgical tasks. In an endoscopic surgical procedure, small incisions, called portals, are made in the patient. An endoscope, which is a device that allows medical personnel to view the surgical site, is inserted in one of the portals. Surgical instruments used to perform specific surgical tasks are inserted into other portals. The surgeon views the surgical site through the endoscope to determine how to manipulate the surgical instruments in order to accomplish the surgical procedure. An advantage of performing endoscopic surgery is that, since the portions of the body that are cut open are minimized, the portions of the body that need to heal after surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

Many tube devices have been developed for use in surgical procedures. They are valuable because they facilitate reduced incision size, improved access and visibility, while enhancing surgical outcome and quicker recovery. Some are cutting devices having either two tubes, one within another, or a single tube with a cutting window. Such cutting devices may be an ear, nose, and throat (ENT) shaver devices.

Clogging of ENT shaver devices is a common annoyance during endoscopic sinus surgery. A common cause of clogging is the trapping of sinus bone and tissue at the distal tip of the ENT shaver device just proximal of a cutting window. Another common cause of clogging is the trapping of sinus bone and tissue just proximal the tube(s) of the cutting device.

A surgical instrument that overcomes these challenges is desired.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
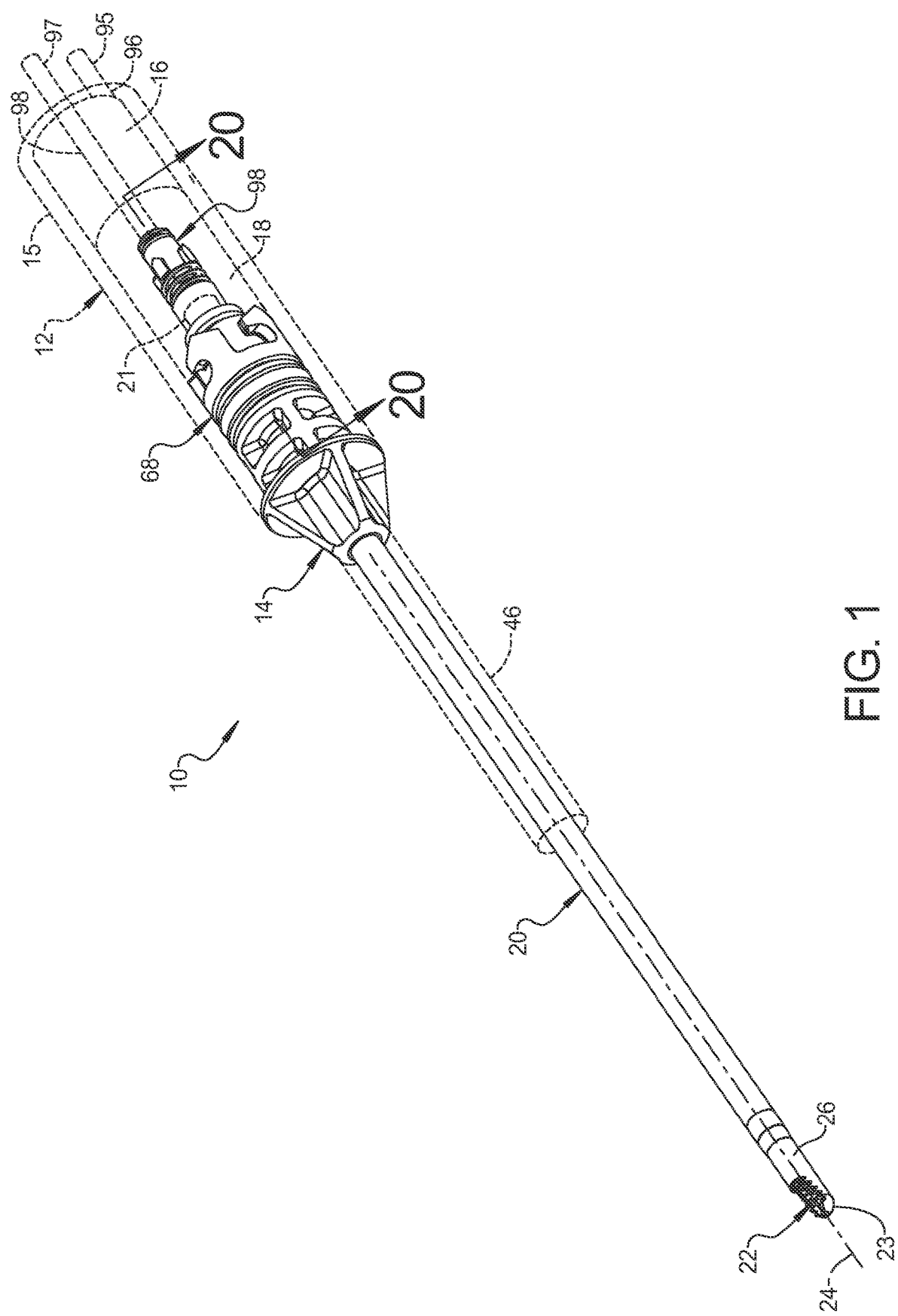
FIG. 1 is a perspective view of a surgical instrument according to an exemplary embodiment of the present disclosure.

Referring to FIG. 1, one embodiment of a surgical instrument 10, according to the present disclosure, is shown for use in a medical procedure for a patient (not shown). In one embodiment, the surgical instrument 10 is an ENT shaver that is disposable and used for resecting sinus bone and tissue during endoscopic sinus surgery. As illustrated, the surgical instrument 10 includes a drive assembly, generally indicated at 12 and shown in phantom lines, and a cutting assembly, generally indicated at 14, removably coupled to the drive assembly 12. The drive assembly 12 is used to rotate a portion of the cutting assembly 14 to remove tissue, bone, etc. from a surgical site of the patient. It should be appreciated that the surgical instrument 10 may be operated by a user (not shown) such as a surgeon.

As illustrated in FIG. 1, the drive assembly 12 includes a housing 15 extending axially. The housing 15 is generally cylindrical in shape. The drive assembly 12 also includes a motor 16 disposed in the housing 15 and having a rotatable drive element 18 coupled to the cutting assembly 14. The motor 16 may be of an electric or pneumatic type. In one embodiment, the drive element 18 is removably coupled to the cutting assembly 14.

It should be appreciated that, in one embodiment, the cutting assembly 14 may be free of any motor. Thus, the cutting assembly 14 may be configured to be disposable after a single-use, or series of uses. Because the cutting assembly 14 may not include any motors, the cost of the cutting assembly 14 may be reduced.

Referring to FIGS. 1-7, the cutting assembly 14 includes a plurality of tubes or tube assembly, generally indicated at 20, extending axially between a distal end 23 and a proximal end 21 (FIG. 20) opposite the distal end 23. The tube assembly 20 has a longitudinal axis 24 defined between the proximal end 21 and the distal end 23. The tube assembly 20 includes a window 22, for example, a cutting window, near or at the distal end 23 with the cutting window 22 adapted to be applied to a surgical site of a patient. In certain embodiments, the tube assembly 20 includes a first, or outer, tube 26 and a second, or inner, tube 28. The inner tube 28 is coupled to the drive assembly 102 and rotatable by the drive element 18 relative to the outer tube 26. The inner tube 28 may be removably coupled to the drive element 18, for example, in an embodiment where the cutting assembly 14 is disposable after a single-use or series of uses.

In one embodiment, the outer tube 26 is non-rotatable and the inner tube 28 is rotatable relative to the outer tube 26. The inner tube 28 and has a lumen 30 extending between the proximal end 21 and the distal end 23 of the tube assembly 20. The inner tube 28 may comprise a proximal region 32 and a distal region 34 to be described. The inner tube 28 comprises, forms, or defines a first or inner cutting window 36 at or near the distal end 23 of the tube assembly 20, such as within the distal region 34 of the inner tube 28.

Each of the inner tube 28 and the outer tube 26 may be generally hollow cylinders extending axially and have a generally circular cross-sectional shape. The outer tube 26 has a diameter greater than a diameter of the inner tube 28 such that the inner tube 28 is disposed within the outer tube 26. In other words, the outer tube 26 has a lumen extending between the proximal end 21 and the distal end 23 of the tube assembly 20 with the inner tube 28 at least partially disposed within the lumen of the outer tube 26. In one embodiment to be described (see FIG. 20), the inner tube 28 has an axial length longer than an axial length of the outer tube 26 such that the inner tube 28 extends past a proximal region 38 of the outer tube 26 when the inner tube 28 is disposed within the outer tube 26.

Figure 2:
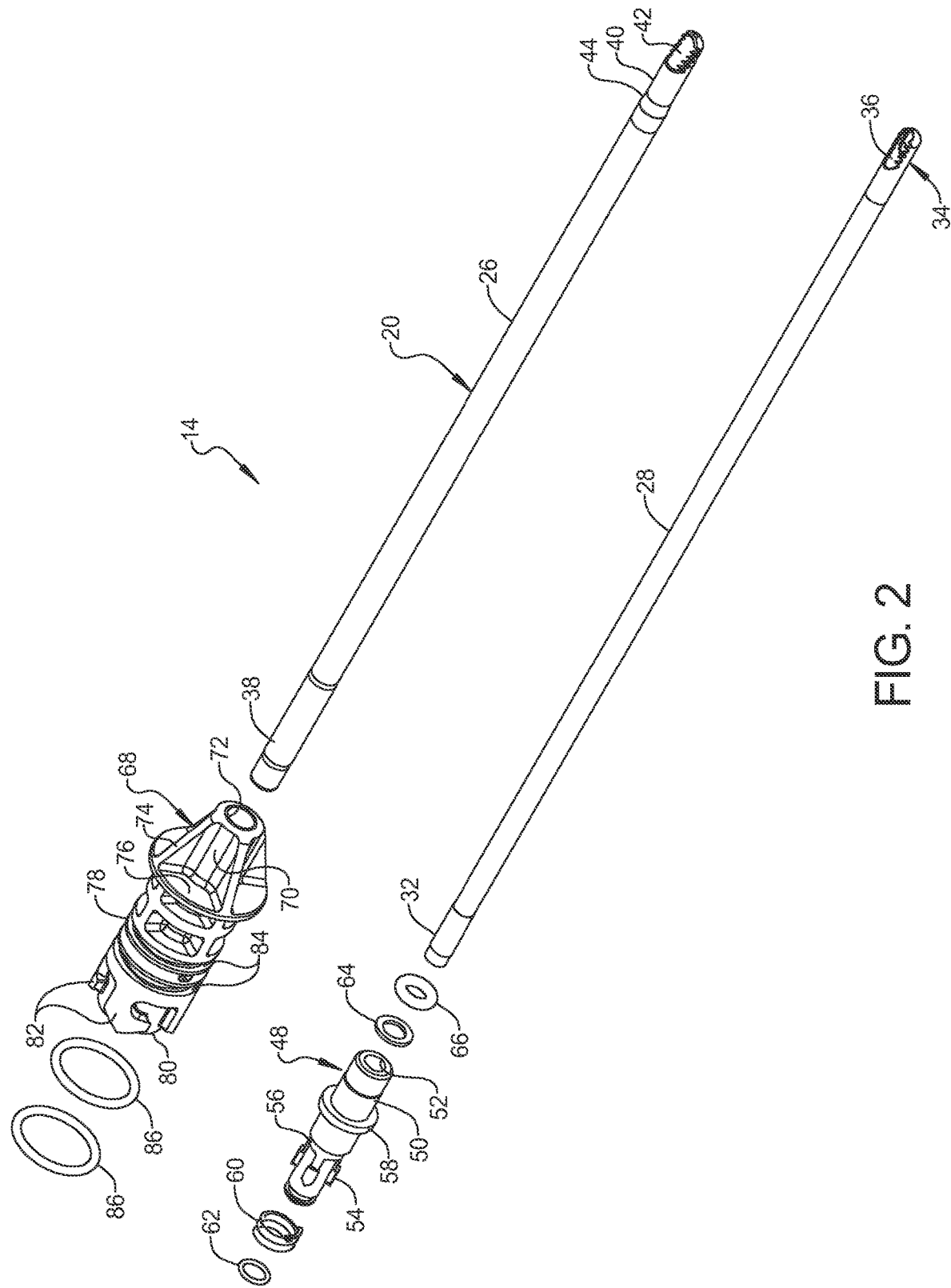
FIG. 2 is an exploded perspective view of the surgical instrument of FIG. 1 with a drive assembly removed.

The outer tube 26 may comprise the proximal region 38 and a distal region 40 as shown in FIG. 2. The outer tube 26 forms a second or outer cutting window 42 at or near the distal end 23 of the tube assembly, such as within the distal region 40 of the outer tube 26. The inner cutting window 36 and the outer cutting window 42 define the cutting window 22 of the tube assembly 20. In one exemplary embodiment, the outer tube 26 may include a radial reduction step 44 within the distal region 34 to allow an outer surface of the inner tube 28 and an inner surface of the outer tube 26 to be close together.

In one embodiment, the tube assembly 20 may further include a non-rotatable sheath or third or covering tube 46 disposed over a portion of the outer tube 26. The covering tube 46 has an axial length less than an axial length of the outer tube 26. The covering tube 46 may be angled, straight, or malleable. It should be appreciated that the covering tube 46 is optional. In addition, it should be appreciated that the covering tube 46 is coupled to a connecting hub 68 to be described. Furthermore, it should be appreciated that any suitable tubing configuration may be utilized so long as the cutting assembly 14 defines the cutting window 22 and can be driven by the drive assembly 12.

The inner tube 28 and outer tube 26 are made of a metal material such as stainless steel or a non-metallic material such as a composite depending on the application. The covering tube 46 may be made of a metal material or a non-metallic material such as a composite depending on the application. It should be appreciated that a wall thickness of the inner tube 28 and the outer tube 26 is relatively thin such as approximately 0.1 to approximately 0.5 millimeters (mm) to allow the tube assembly 20 to be of a relatively small diameter and also to be lightweight. It should also be appreciated that the diameters of the inner tube 28 and the outer tube 26 have a relatively small diameter such as approximately 2.0 mm to approximately 5.0 mm so as to work in a small opening of a nasal cavity or oral cavity of the patient and to prevent the user's view from being obstructed. In one embodiment, the tube assembly 20 may have a bend (not shown) near the distal end 23. It should further be appreciated that the inner tube 28 and the outer tube 26 may be scaled larger or smaller depending on the application.

The cutting assembly 14 also includes a drive hub, generally indicated at 48, disposed about a proximal end of the inner tube 28 to allow the inner tube 28 to be connected to the drive element 18 for rotation of the inner tube 28 about the longitudinal axis 24. The drive hub 48 includes a hub member 50 disposed about the inner tube 28. The hub member 50 extends axially and is generally cylindrical in shape. The hub member 50 has an aperture 52 extending axially at least partially therethrough to receive the inner tube 28 as illustrated in FIG. 2. The hub member 50 may also include a plurality of ridges 54 extending radially and axially and spaced circumferentially thereabout. The hub member 50 may further include a reduced diameter portion 56 adjacent the ridges 54. The reduced diameter portion 56 of the hub member 50 defines a reduced aperture 53 in communication with the aperture 52 with the reduced aperture 53 being smaller in diameter than the aperture 52 (see FIG. 20). The decrease in diameter from the aperture 52 to the reduced aperture 53 forms a lip 55 adapted to be positioned adjacent to or in an abutting relationship with the proximal end 21 of the tube assembly 20 in a manner to be described. The hub member 50 also includes a flange 58 extending radially at a distal end thereof. The hub member 50 may be made of a non-metallic material. The hub member 50 may be integral, unitary, and formed as one-piece.

The drive hub 48 can also include a spring 60 and a seal 62 such as an o-ring disposed about the hub member 50 at a proximal end thereof in the reduced diameter portion 56. The drive hub 48 may include a washer 64 and a seal 66 such as an o-ring at a distal end thereof disposed about the distal end of the inner tube 28. It should be appreciated that the drive hub 48 allows for rotation of the inner tube 28 and may allow for the transfer of fluid through the inner tube 28. It should also be appreciated that a variety of drive coupling configurations may be used with the cutting assembly 14.

The cutting assembly 14 further includes a connecting hub, generally indicated at 68, disposed about the inner tube 28 and a portion of the drive hub 48 to allow the drive assembly 12 to be removably coupled to the cutting assembly 14. The connecting hub 68 includes a housing hub 70 adapted to be engaged by a least a portion of a hand of a user and supporting the outer tube 26 or the covering tube 46. The housing hub 70 includes an aperture 72 extending axially therethrough to receive the outer tube 26 or the covering tube 46. The housing hub 70 may include a plurality of grip members 74 extending radially and axially and a flange 76 extending radially outwardly at one end to support one or more fingers of a hand. The connecting hub 68 also includes a coupling member 78 disposed about the inner tube 28. The coupling member 78 extends axially and is generally cylindrical in shape. The coupling member 70 has an aperture 72 extending axially therethrough to receive the inner tube 28. The coupling member 78 includes a cavity 80 extending axially into the proximal end thereof to receive a distal end of the fluid coupling. The coupling member 78 may include one or more ridges 82 extending radially and spaced circumferentially from each other at the proximal end to be coupled to the housing 15 of the drive assembly 12. The coupling member 78 may include one or more grooves 84 extending radially inward and circumferentially and spaced axially from each other and one or more seals 86 such as o-rings disposed in the grooves 84. The connecting hub 68 is made of a non-metallic material. The connecting hub 68 may be integral, unitary, and formed as one-piece. It should be appreciated that the connecting hub 68 allows for the coupling of the drive assembly 12 to the cutting assembly 14.

Figure 3:
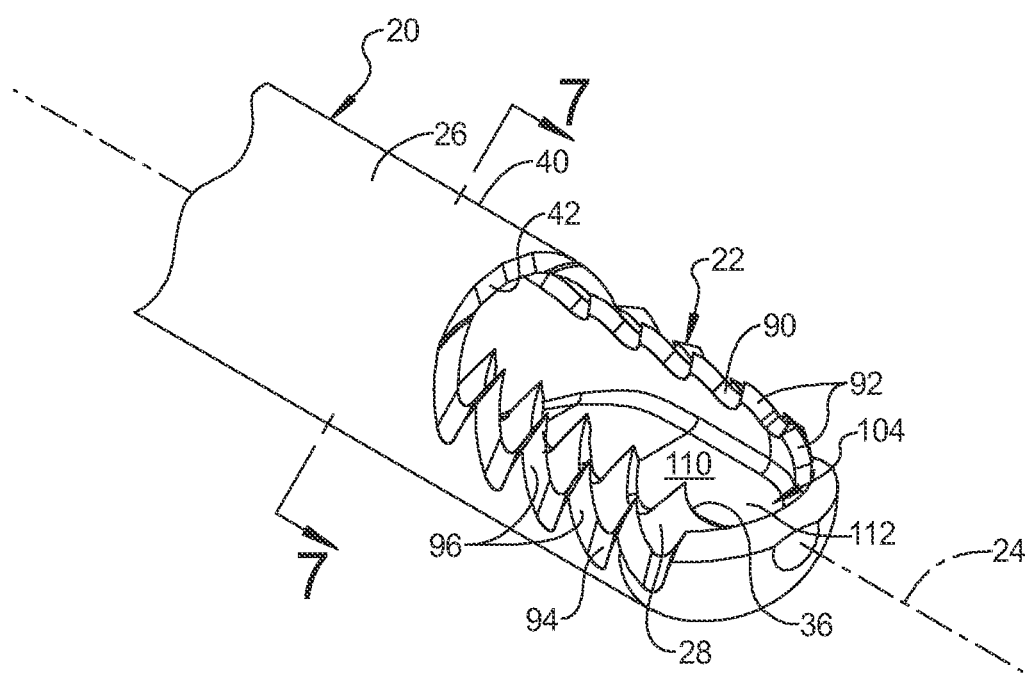
FIG. 3 is a perspective view of a clog-reducing tip of a cutting assembly of the surgical instrument of FIGS. 1 and 2 in accordance with an exemplary embodiment of the present disclosure.

Referring to FIG. 3, the cutting window 22 includes the inner cutting window 36 in the inner tube 28 formed as an opening extending axially and diametrically through a wall on one side near the distal end 23 of the tube assembly 20. The cutting window 22 also includes the outer cutting window 42 in the outer tube 26 formed as an opening extending axially and diametrically through a wall on one side near the distal end 23 of the tube assembly 20. The inner and outer cutting windows 36 and 42 are generally elongated and oval in shape, but may be any suitable shape. The inner cutting window 36 may include at least one or more cutting edges 90. The cutting edge 90 may include a plurality of teeth 92 forming a serrated edge. The outer cutting window 42 may include at least one or more cutting edges 94. The cutting edge 94 may include a plurality of teeth 92 forming a serrated edge. The inner cutting window 36 is adapted to be temporarily aligned radially with the outer cutting window 42 to receive material within the cutting window 22 as the inner tube 28 rotates within the outer tube 26. As the inner tube 28 rotates within the outer tube 26, the inner and outer cutting windows 36 and 42 are removed from radial alignment such that the cutting edges 90 and 94 cut or reduce the material positioned within the cutting window 22 of the tube assembly 20.

In one embodiment illustrated in FIG. 1, the surgical instrument 10 includes an irrigation connection 95 on the housing 15 for connection to a fluid source and an irrigation path or passage 96 extending through the housing 15 between the irrigation connection 95 and the cutting assembly 14 and between the inner tube 28 and the outer tube 26 to the cutting window 22 to provide lubrication. The surgical instrument 10 also includes an aspiration or suction connection 97 on the housing 15 for connection to a suction source and an aspiration or suction path or passage 98 extending through the housing 15 between the suction connection 97 and the first cutting window 36 of the inner tube 28.

Figure 4:
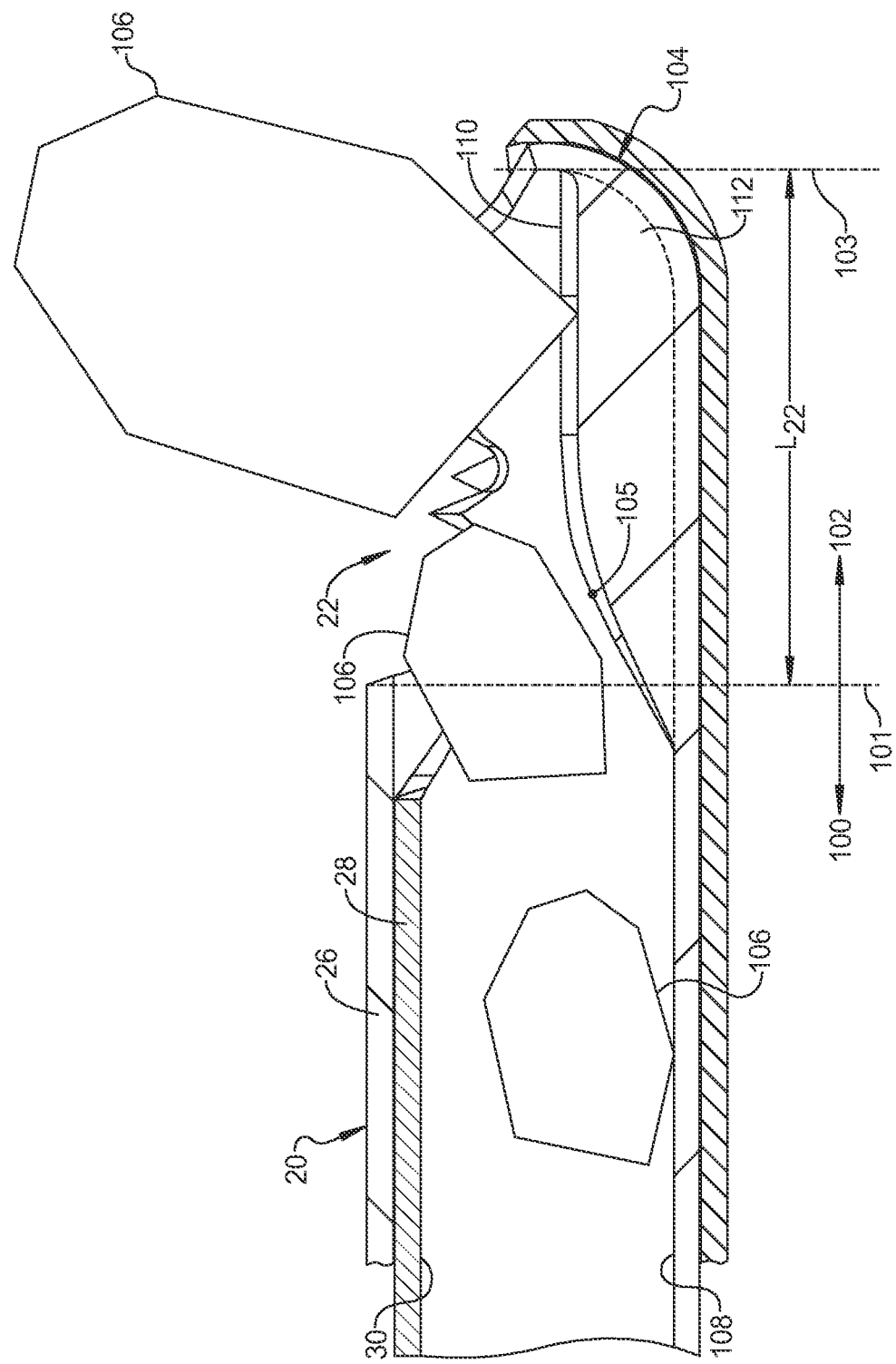
FIG. 4 is a fragmentary elevational view of the clog-reducing tip of the cutting assembly of FIG. 3 with removed material represented schematically.
Figure 5:
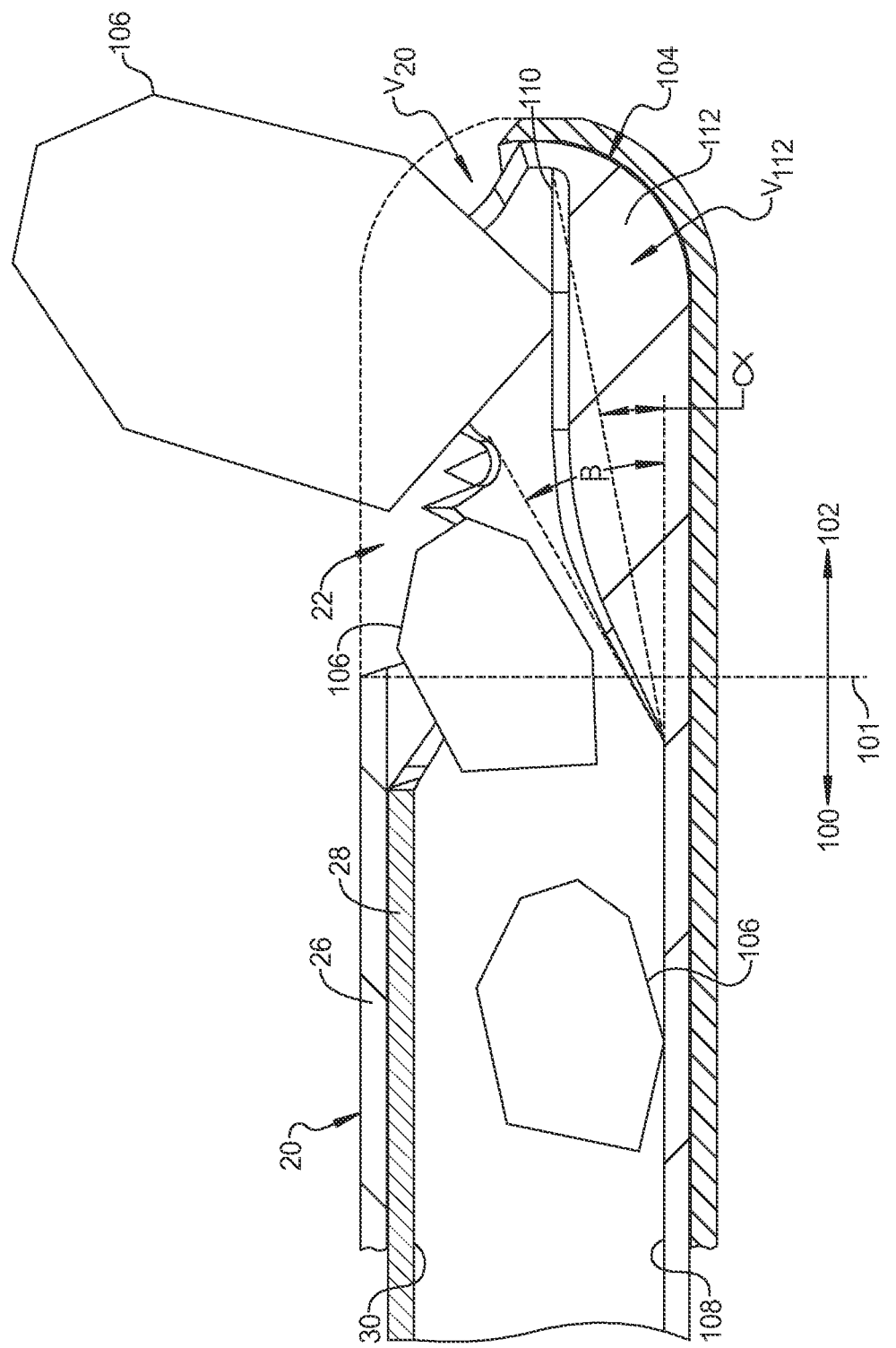
FIG. 5 is another fragmentary elevational view of the clog-reducing tip of the cutting assembly of FIG. 3.
Figure 6:
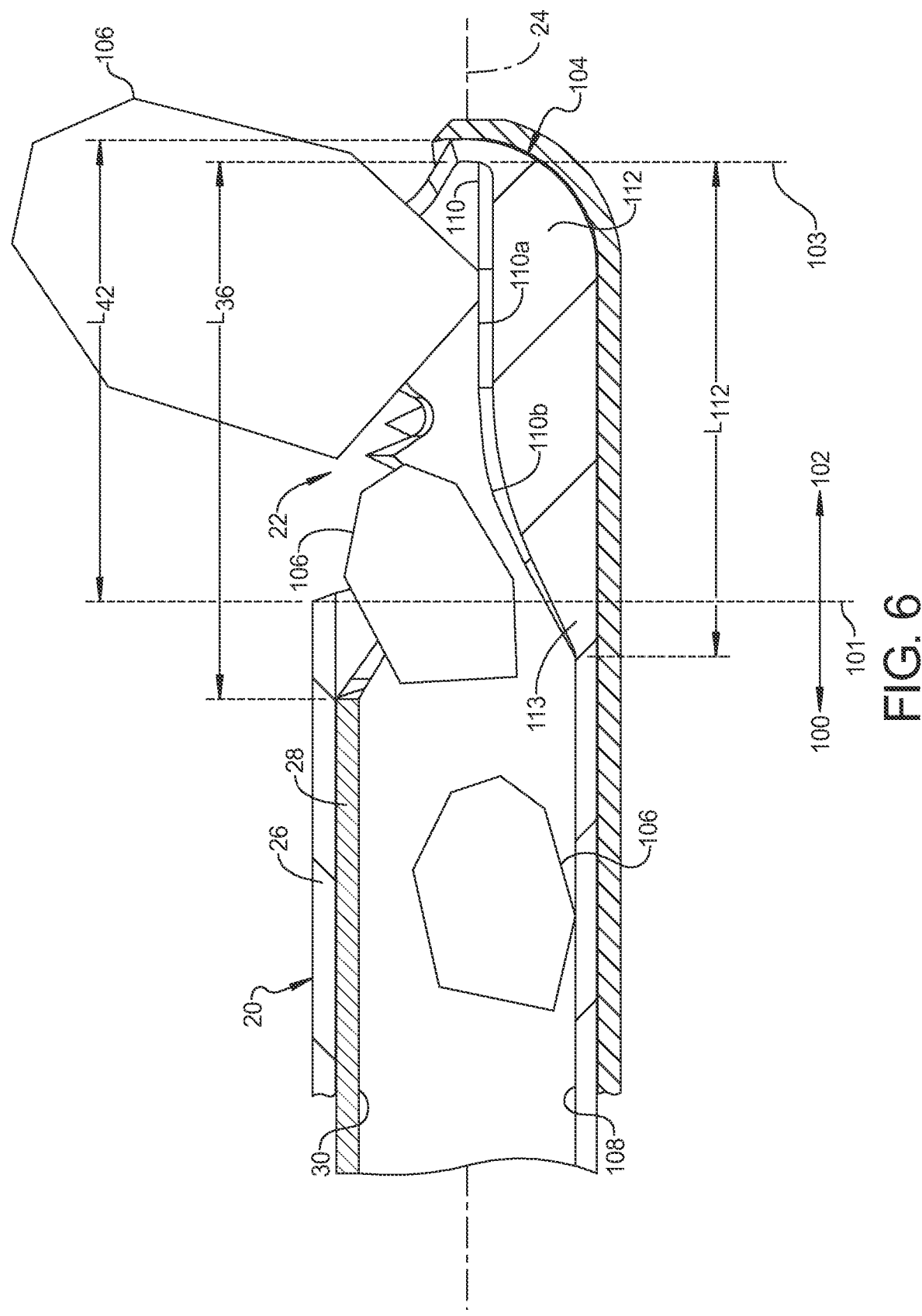
FIG. 6 is another fragmentary elevational view of the clog-reducing tip of the cutting assembly of FIG. 3.

FIGS. 4-6 show fragmentary elevational views of a clog-reducing tip, generally indicated at 104, in accordance with an exemplary embodiment of the present disclosure. Referring first to FIG. 4, the cutting window 22 of the tube assembly 20 comprises a distal boundary 103 and a proximal boundary 101 opposite the distal boundary 103. In one embodiment, the boundaries 101 and 103 may be defined as an imaginary plane extending perpendicularly to the longitudinal axis 24 of the tube assembly 20 at a proximal-most point and a distal-most point of the cutting window 22, respectively. Thus, in the exemplary embodiment illustrated in FIG. 4, the outer tube 26 projects distal to the inner tube 28 to define the proximal boundary 101 of the cutting window 22, and the distal end 23 the inner tube 28 is positioned proximally (i.e., within) the outer tube 26 to define the distal boundary 103 of the cutting window 22. Stated differently, the proximal and distal boundaries 101 and 103 may be considered the proximal-most and distal-most points of the cutting window 22, respectively, when the cutting window 22 is viewed in plan. In certain embodiments, a portion of the inner tube 28 distal to the proximal boundary 101 of the cutting window 22 defines the distal region 34 of the inner tube 28.

As illustrated in FIG. 4, the clog-reducing tip 104 of the tube assembly 20 comprises a projection 112 within the lumen 30 of the inner tube 28. The projection 112 is adapted to reduce the size of material removable through the cutting window 22, thereby reducing clogging of the tube assembly 20. In certain embodiments, at least a portion of the projection 112 is positioned distal to the proximal boundary 101 (in a direction of arrow 102 in FIG. 4) to provide a reduced cross sectional area to said lumen 30 relative to the cross sectional area of the lumen 30 proximal to the projection 112. For another example, the projection 112 occupies a volume $V_{112}$ (FIG. 5) within the distal region 34 of the inner tube 28. The projection 112 reduces the amount by which material 106 to be removed may penetrate the cutting window 22. Consequently, the cutting action from rotating the inner tube 28 within the outer tube 26 (via the cutting edges 90 and 94) reduces the material 106 into sufficiently small bits before the material 106 may pass within the lumen 30 proximal to the cutting window 22, thereby decreasing the likelihood of clogging of the tube assembly 20.

In certain embodiments, the reduced cross sectional area of the lumen 30 may defined as the difference between the cross sectional area of the lumen 30 (e.g., $\pi*d$ with d being the diameter of the lumen 30) and a cross sectional area of the projection 112. In one example, a ratio of the reduced cross sectional area of the lumen 30 to the cross sectional area of the lumen 30 is within the range of 1:1.1 to 1:2.0, and more particularly within the range 1:1.3 to 1:1.8, and even more particularly within the range of 1:1.5 to 1:1.6. The reduced cross sectional is adapted to ensure that no dimension of material 106 (e.g., bone and/or tissue chip) is larger than the cross sectional area of the lumen 30, and more particularly less than the cross sectional area of the lumen 30 by a predetermined factor based on the ratio described above. In other exemplary embodiments, the volume $V_{112}$ of the projection 112 disposed within the distal region 34 occupies within the range of 10%-70% of a volume $V_{20}$ of the distal region 34 of the tube assembly 20, and more particularly within the range of 20%-60% of the volume $V_{20}$ of the distal region 34 (see FIG. 5).

In one exemplary operation of a conventional ENT shaver, the material is able to penetrate the cutting window to contact the inner tube opposite the cutting window such that the size of the reduced material is approximately equal to the diameter of the lumen. The reduced material having a size approximately equal to the diameter of the lumen increases the likelihood of the reduced material clogging within the lumen, particularly near the cutting window. Furthermore, in instances where the axial length of the cutting window is greater than the diameter of the lumen, the likelihood of the reduced material clogging is further increased in conventional ENT shavers.

The clog-reducing tip 104 of the present disclosure significantly reduces the likelihood of clogging by, for example, providing that the distance from the proximal boundary 101 of the cutting window 22 at the outer tube 26 to a nearest point on the projection 112 (approximated as point 105 as shown in FIG. 4) is less than the diameter of the lumen 30. Thus, any reduced material 106 that may pass through the "throat" (i.e., the distance from cutting window 22 to the nearest point 105) has a size smaller than the diameter of the lumen 30 itself. Consequently, once the reduced material reaches the lumen 30 proximal to the projection 112, it is increasingly unlikely that the reduced material clogs the tube assembly 20.

Prior to the material being sufficiently reduced to pass through the "throat" of the inner tube 28, the projection 112 (and the proximal boundary 101 of the cutting window 22) maintains the material 106 in a position such that the cutting action continues to reduce the material 106 with each rotation of the inner tube 28. Despite the material 106 possibly remaining positioned near the cutting window 22 for increased time, empirical investigations have shown minimal effect on material removal capacity of the tube assembly 20 incorporating the clog-reducing tip 104 with near or total elimination of clogging commonly associated with conventional ENT shavers.

With continued reference to FIG. 4 and concurrent reference to FIG. 6, the projection 112 may extend within the lumen 30 from near the distal end 23 of the tube assembly 20 to a position proximal to (i.e., in the direction of arrow 100) the proximal boundary 101. In other words, another portion 113 of the projection 112 may be positioned proximal to the proximal boundary 101. In other words, the axial length $L_{112}$ of the projection 112 may be greater than the axial length $L_{22}$ of the cutting window 22. Positioning the portion 113 of the projection 112 proximal to the proximal boundary 101 ensures that the material 106 passing through the proximal boundary 101 is reduced to a size less than the cross sectional area of the lumen 30 of the tube assembly 20. It is understood that the axial length $L_{12}$ of the projection 112 may be greater than an axial length $L_{42}$ of the outer cutting window 42 and/or less than an axial length $L_{36}$ of the inner cutting window 36. In certain embodiments, the projection 112 may extend even more proximally to the proximal boundary 101 than shown in FIGS. 4 and 6 with a proximal second portion 110b to be described having a shallower taper.

The projection 112 of the clog-reducing tip 104 has a shelf or an inner surface 110. The inner surface 110 is displaced radially inward relative to an interior surface 108 of the lumen 30 (i.e., proximal to the projection 112) towards the longitudinal axis 24 of the tube assembly 20. Referring to FIG. 5, the projection 112 may be angled relative to the interior surface 108 of the lumen 30. For example, a line extending between distal and proximal ends of the projection 112 may be oriented at an angle α in the range of approximately 5 degrees to approximately 40 degrees relative to the interior surface 108 of the lumen 30. In other embodiments, the angle α is between approximately 10 degrees and approximately 30 degrees, and more particularly between approximately 15 degrees and approximately 25 degrees. The angle α generally provides a profile (when viewed in elevation as shown in FIGS. 4-6) to the projection 112 that tapers in the direction of arrow 100. In other words, a distance from the longitudinal axis 24 to the projection 112 at the distal boundary 103 of the cutting window 22 is less than a distance from the longitudinal axis 24 from the projection 112 at the proximal boundary 101 of the cutting window 22 such that the projection 112 tapers in the direction towards the proximal boundary 101. The tapering of the projection 112 advantageously maintains the material 106 near the distal boundary 103 closer to the cutting edges 90 and 94 to reduces the material 106 into smaller bits as the reduced material 106 moves along the inner surface 110 of the projection 112 towards the lumen 30 proximal to the cutting window 22. The tapering of the projection 112 also ensures a gradual transition through the "throat," as previously described, such that reduced material 106 passing through the "throat" immediately encounters a greater cross sectional area of the lumen 30 and is quickly urged proximally within the lumen 30 under forces from the suction source.

In certain embodiments, the inner surface 110 of the projection 112 further comprises or is defined by a distal first portion 110a and the proximal second portion 110b proximal to the distal first portion 110a. Referring to FIGS. 5 and 6. The distal first portion 110a may be oriented substantially parallel to the longitudinal axis 24 of the tube assembly 20. The distal first portion 110a may be substantially planar when viewed in elevation. The proximal second portion 110b may be sloped or angled relative to the distal first portion 110a and the interior surface 108 of the lumen 30. The proximal second portion 110b may be arcuate when viewed in elevation to provide a smooth transition to the distal first portion 110a. The proximal second portion 110b may be oriented at an angle β in the range of approximately 20 degrees to approximately 60 degrees relative to the interior surface 108 of the lumen 30. In other embodiments, the angle β is between approximately 30 degrees and approximately 50 degrees.

Figure 7:
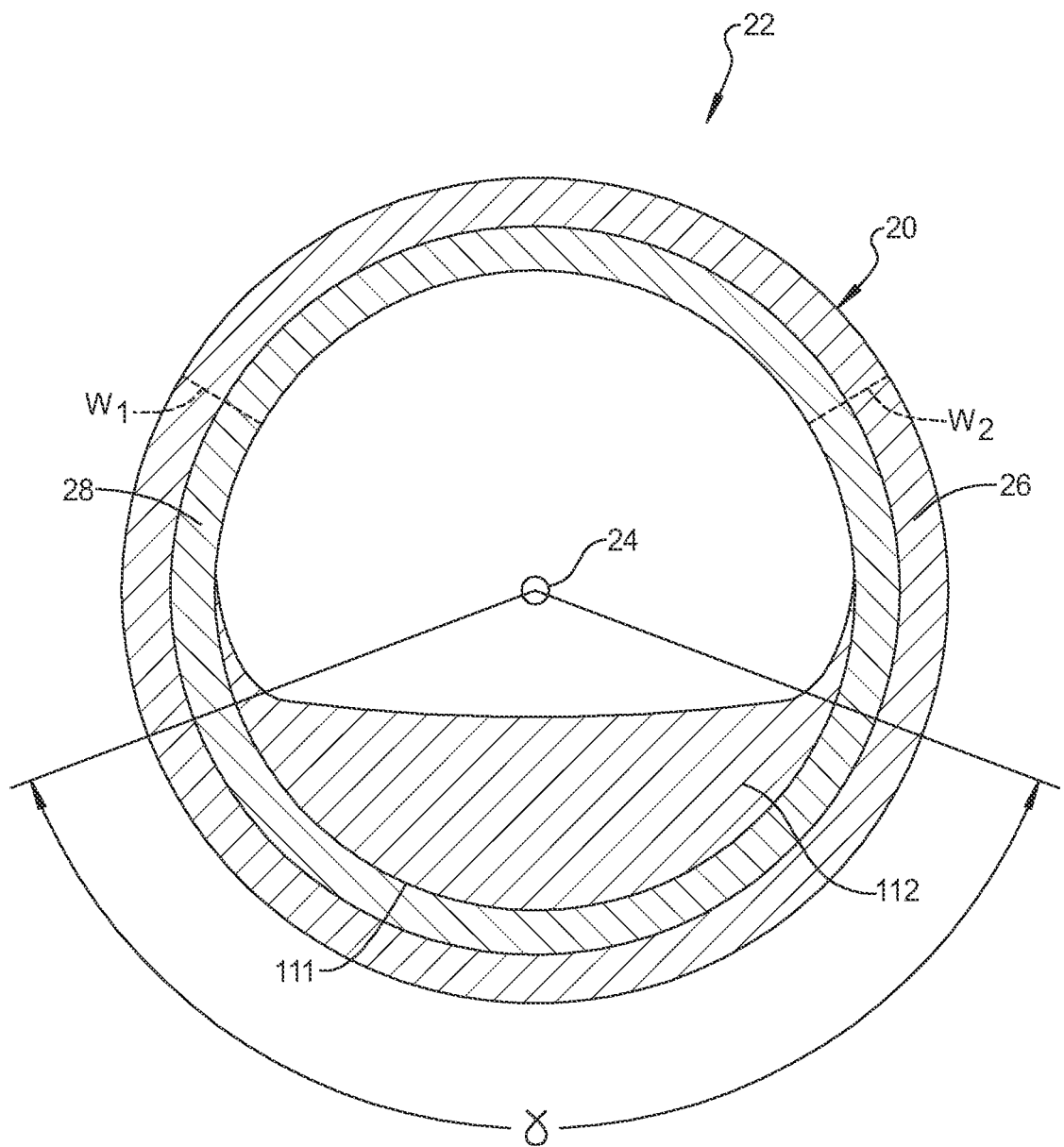
FIG. 7 a cross-sectional view of the cutting assembly of FIG. 3 taken along lines 7-7.
Figure 8:
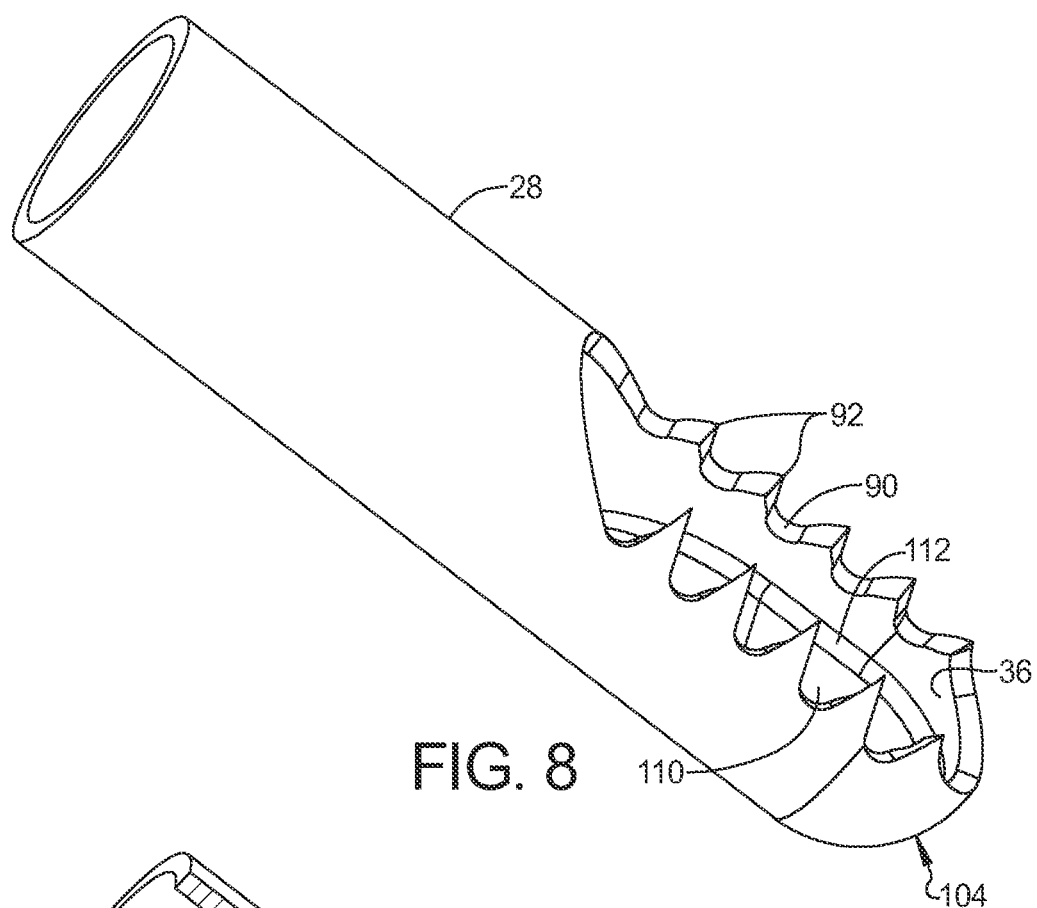
FIG. 8 is a perspective view of the clog-reducing tip according to another exemplary embodiment of the present disclosure.
Figure 9:
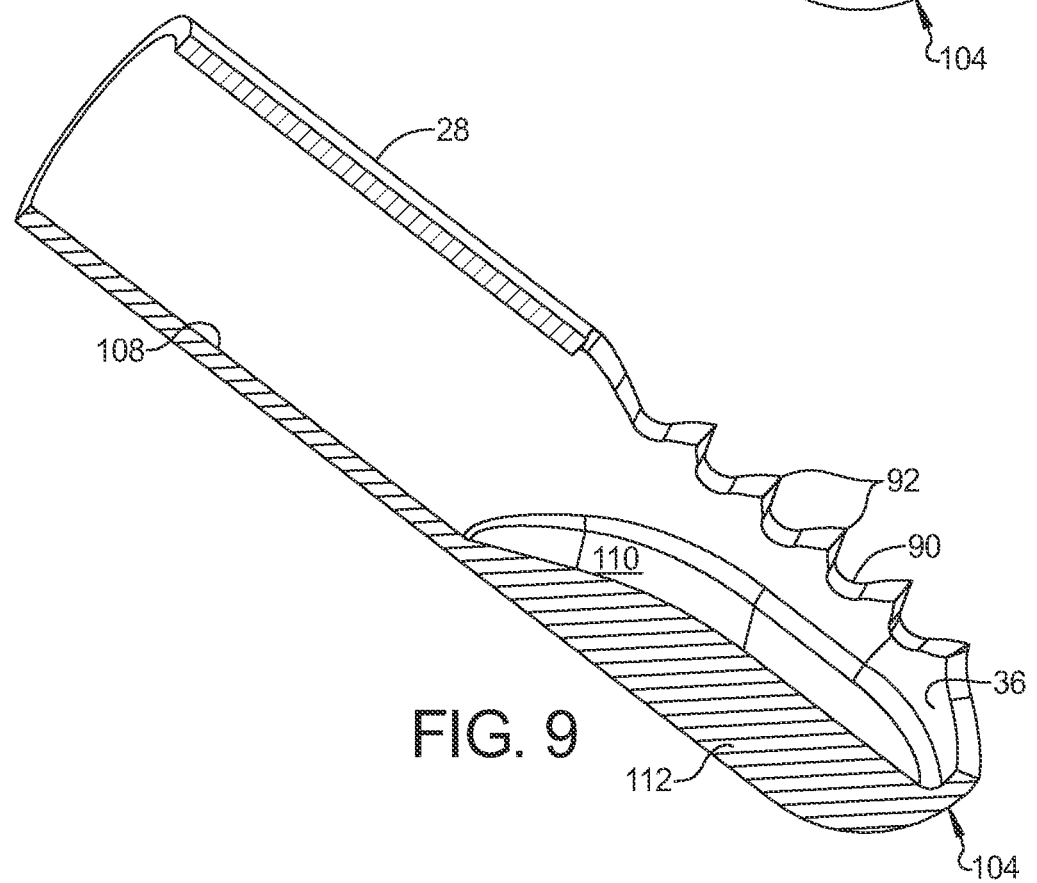
FIG. 9 is fragmentary perspective view of the clog-reducing tip of FIG. 8.

Referring to FIG. 7, the projection 112 may be positioned about the longitudinal axis 24 radially opposite the cutting window 22 of the tube assembly 20, and more particularly radially opposite the inner cutting window 36. With the projection 112 within the lumen 30 of the inner tube 28, the relative positioning between the projection 112 and the inner cutting window 36 remains constant as the inner tube 28 rotates within the outer tube 26. The radial position of the cutting window 22 of FIG. 7 is approximated between lines W1 and W2 with the projection 112 being positioned about the longitudinal axis 24 substantially opposite the space between lines W1 and W2.

The projection 112 is positioned about a circumference of the lumen 30 in a manner sufficient to suitably reduce the material 106 to prevent clogging of the tube assembly 20. In certain embodiments, the projection 112 is positioned about less than one half of the circumference of the lumen 30. For example, the axial cross sectional view FIG. 7 shows one side of the projection 112 radially positioned approximately at the 4 o'clock position, and another side of the projection 112 radially positioned approximately at the 8 o'clock position. Stated differently, an angle γ about the longitudinal axis 24 and extending between opposing sides of the projection 112 within the range of approximately 70 degrees to approximately 180 degrees, and more particularly with the range of approximately 90 degrees to approximately 160 degrees, and even more particularly with the range of approximately 110 degrees to approximately 150 degrees. Other suitable values for the angle γ are contemplated based on, at least in part, the diameter of the lumen 30, the intended application of the surgical instrument 10, and the like.

In certain embodiments, the clog-reducing tip 104 includes an insert secured within the lumen 30 of the inner tube 28. The insert defines the projection 112 and forms the inner surface 110. For example, the insert may be bonded to the lumen 30 of the inner tube 28. The insert may include an outer surface 111 and the inner surface 110 with the outer surface 111 shaped to conform a portion of the lumen 30 (see FIG. 7). The inner surface 110 may define the projection 112. The insert may have a thickness defined between the inner surface 110 and the outer surface 111 with the thickness of the insert tapering in an axial direction; i.e., the direction 100 towards the proximal boundary 101 of the cutting window 22. It is also understood that the thickness of the insert may taper radially about the longitudinal axis 24 of the tube assembly 20, as shown in FIG. 7.

Figure 10:
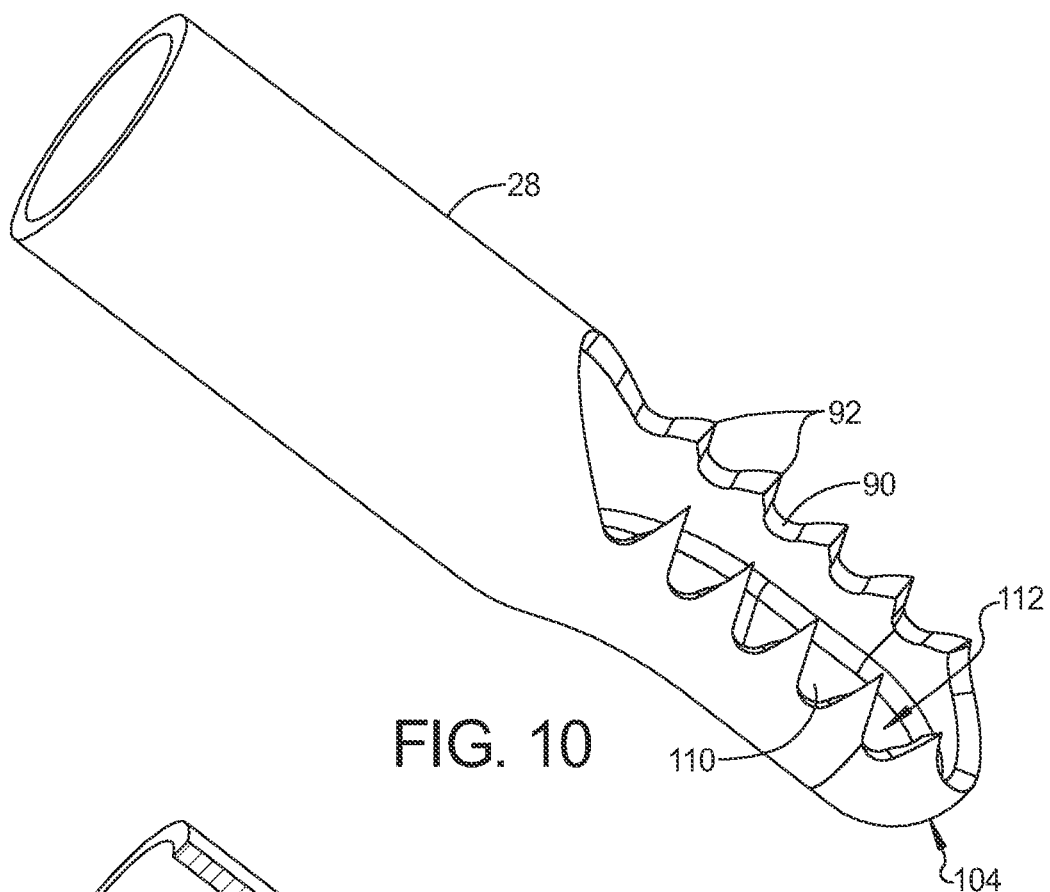
FIG. 10 is a perspective view of the clog-reducing tip according to another exemplary embodiment of the present disclosure.
Figure 11:
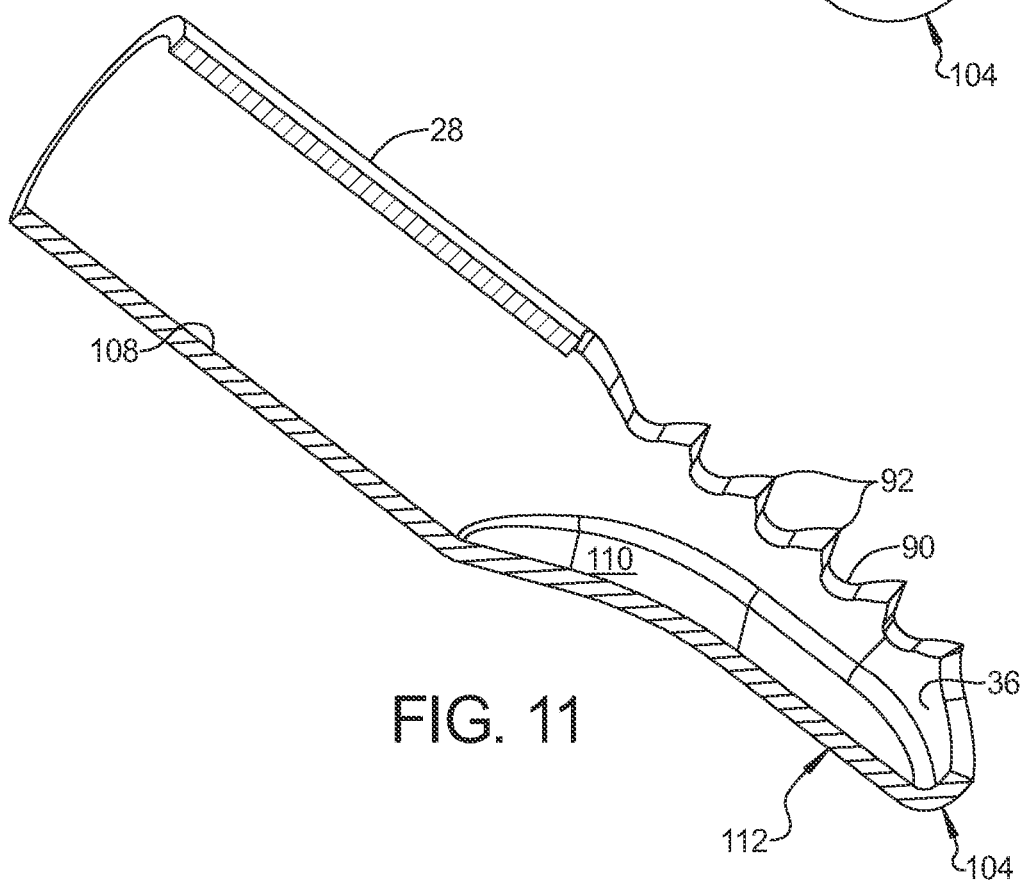
FIG. 11 is fragmentary perspective view of the clog-reducing tip of FIG. 10.
Figure 12:
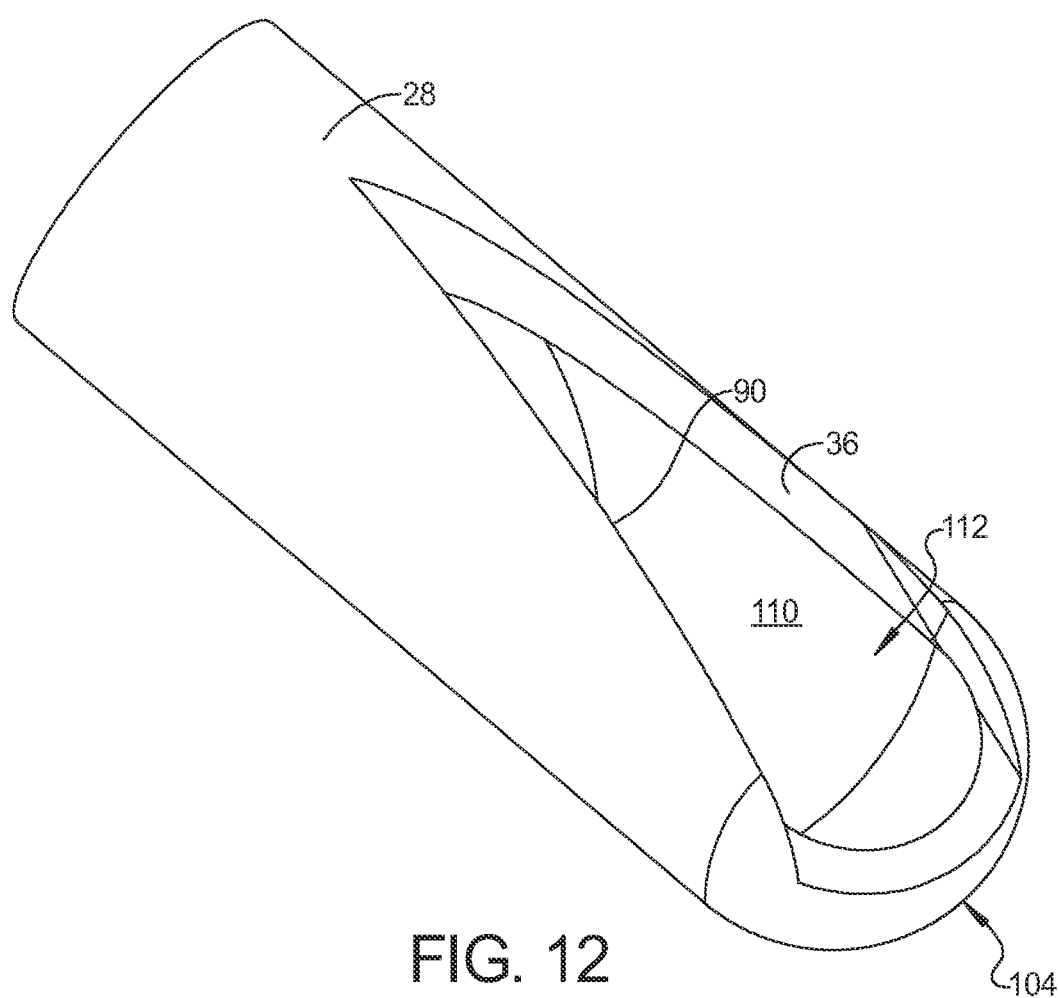
FIG. 12 is a perspective view of the clog-reducing tip according to another exemplary embodiment of the present disclosure.
Figure 13:
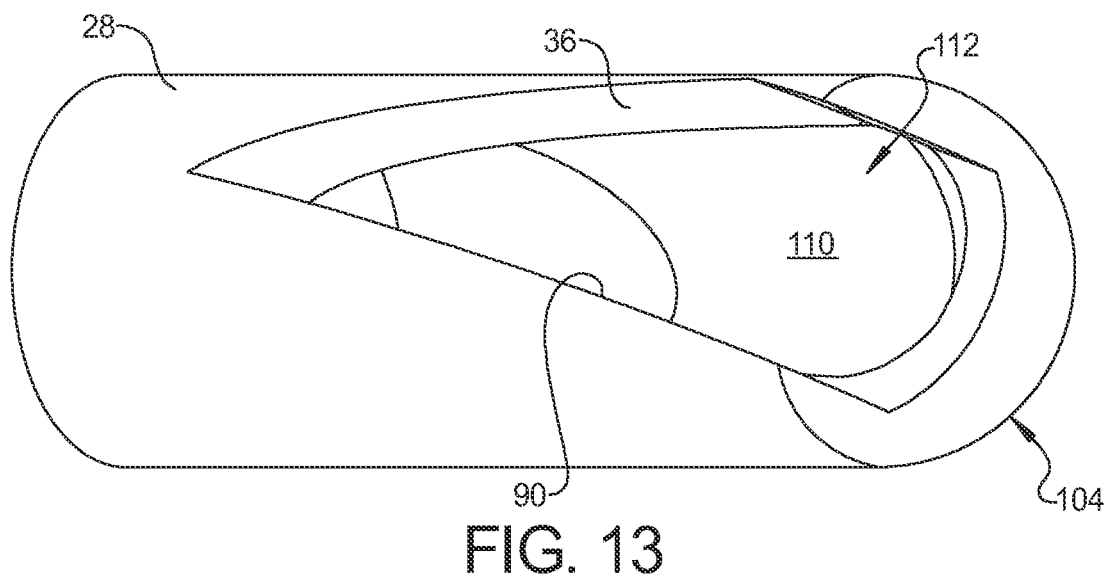
FIG. 13 is elevational view of the clog-reducing tip of FIG. 12.
Figure 14:
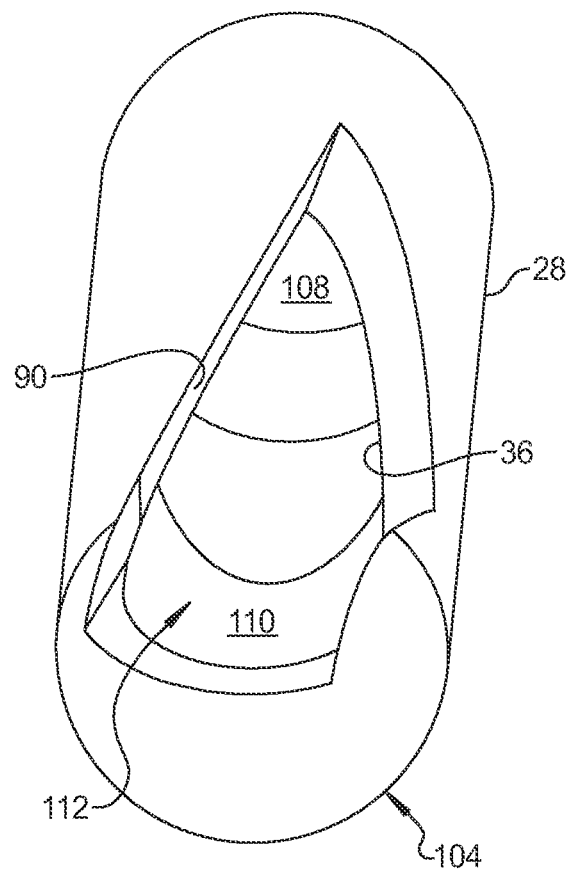
FIG. 14 is an angled view of the clog-reducing tip of FIG. 12.
Figure 15:
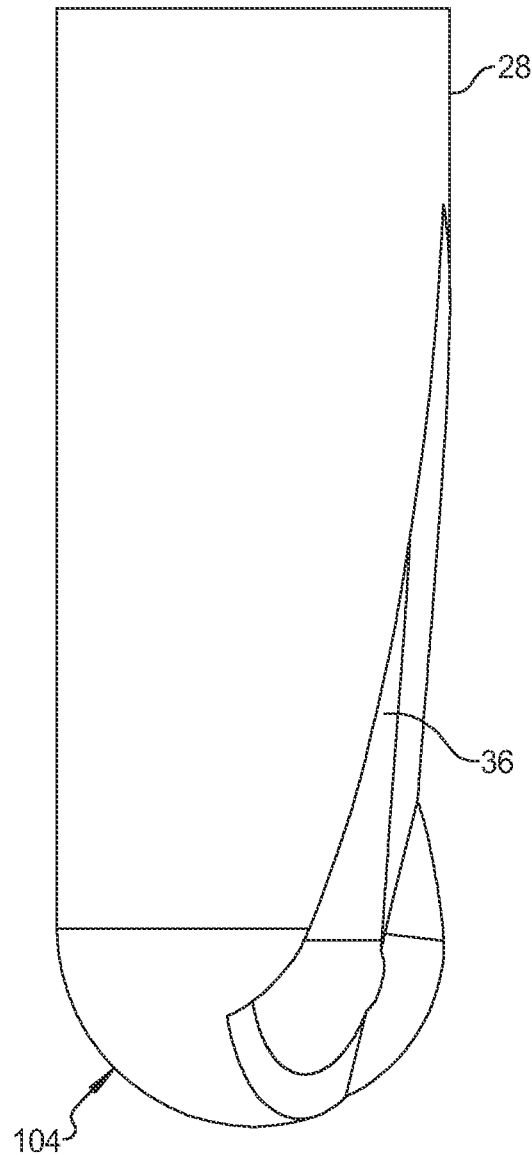
FIG. 15 is a plan view of the clog-reducing tip of FIG. 12.
Figure 16:
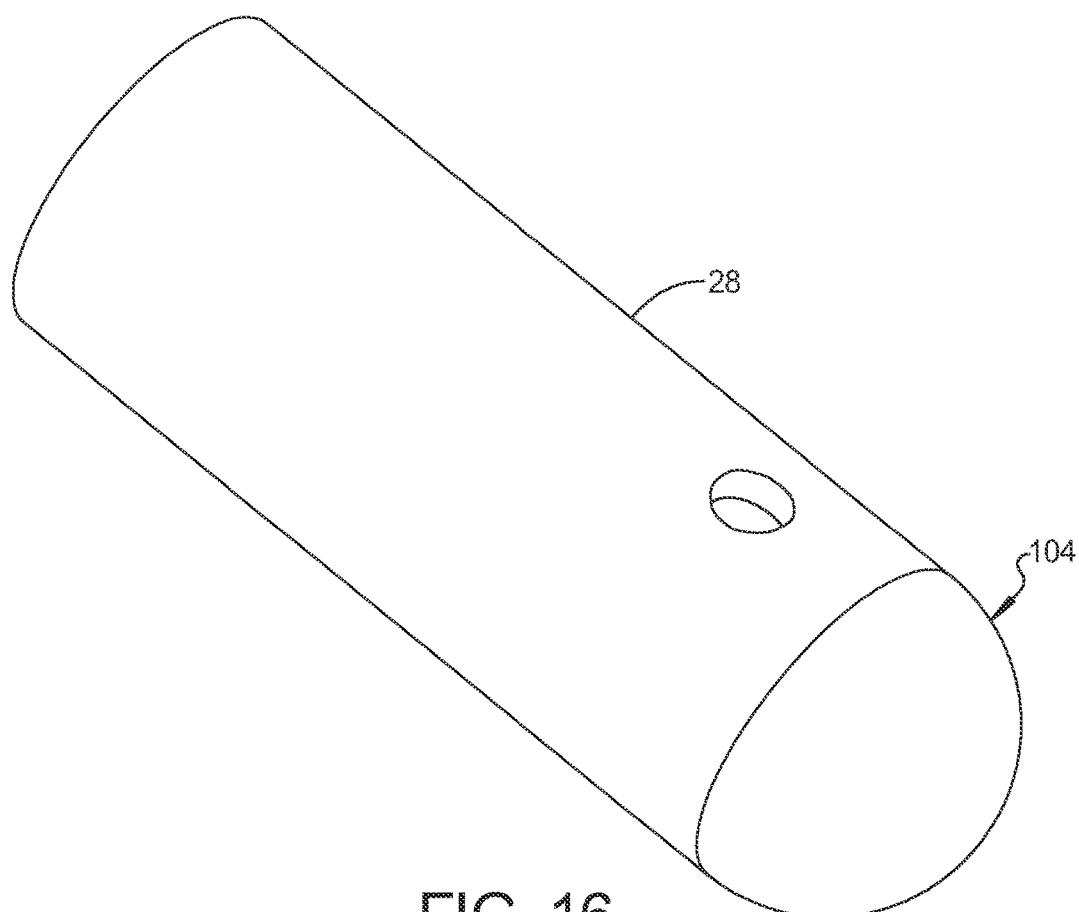
FIGS. 16-19 are diagrammatic views illustrating a machined process for forming the clog-reducing tip of FIGS. 12-15.
Figure 17:
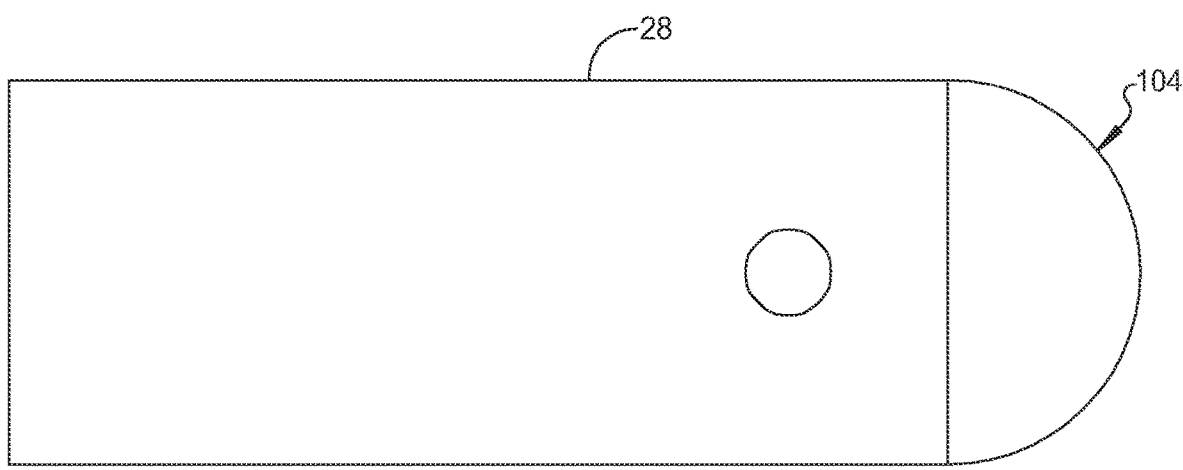
Figure 18:
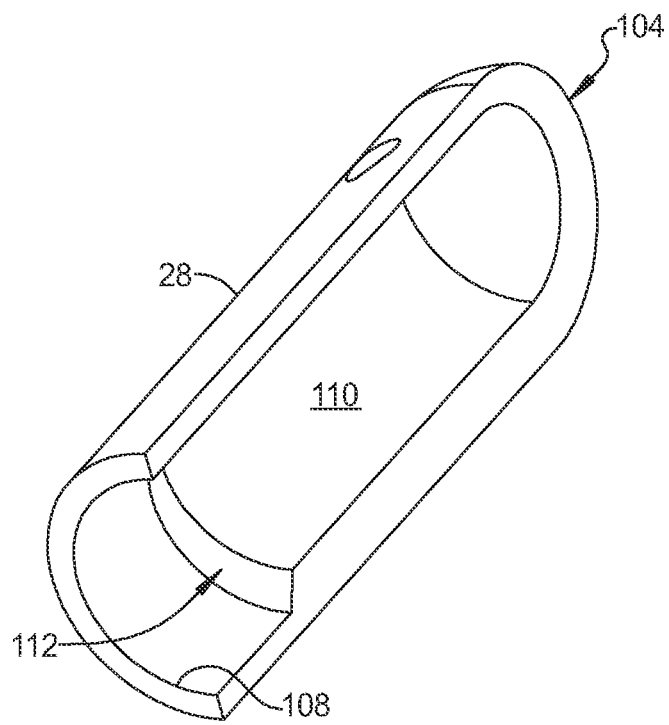
Figure 19:
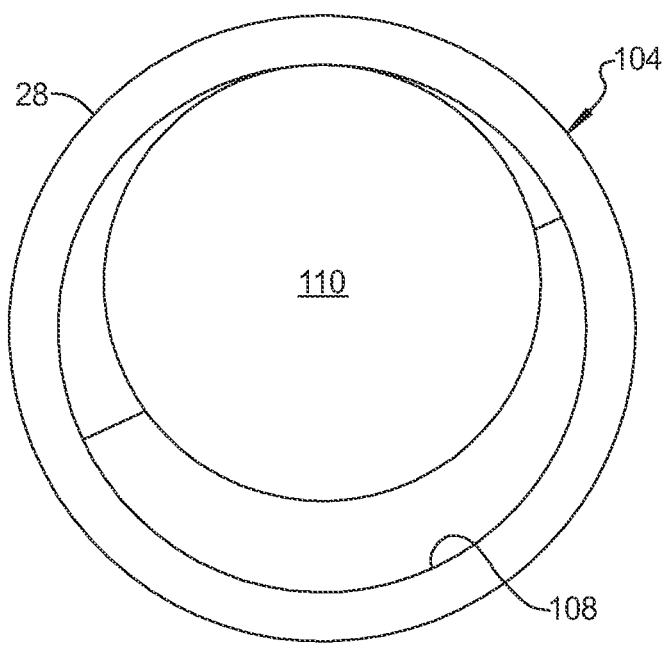

In another exemplary embodiment of the clog-reducing tip 104 illustrated in FIGS. 10 and 11, the projection 112 is defined by the lumen 30 distal to the proximal boundary 101 being formed radially inwardly towards the longitudinal axis 24. In other words, whereas the projection 112 of FIGS. 4-6 are within the lumen 30 with the inner tube 28 having a generally cylindrical outer profile to the distal end 23 of the tube assembly 20, the FIGS. 10 and 11 show the inner tube 28 near the distal end 23 (e.g., the distal region 34) deformed inwardly towards the longitudinal axis 24. With a portion of the inner tube 28 deformed inwardly, the lumen 30 of the inner tube 28 is corresponding deformed inwardly and consequently defines the projection 112 providing the reduced cross sectional area of the lumen 30 as previously described. The inwardly deformed portion of the inner tube 28 may be constructed through stamping, drawing, or similarly suitable manufacturing process.

Referring to FIGS. 12-15, yet another embodiment, according to the present disclosure, of the clog-reducing tip 104 is shown. In this embodiment, the clog-reducing tip 104 includes the inner surface 110 formed by boring out an eccentric borehole within the distal region 34 of the inner tube 28. The borehole is eccentric with respect to the longitudinal axis 24 of the tube assembly 20. The eccentric borehole is in communication with the cutting window 22 and the lumen 30 of the inner tube 28. This type of tip would typically be machined. As illustrated, the inner surface 110 has a smaller cross-section at the first cutting window 36. The process of machining the clog-reducing tip 104 is illustrated in FIGS. 16-19.

The present disclosure provides a method, according to one embodiment of the present disclosure, for operating the surgical instrument 10 on a patient. The method includes the steps of providing the cutting assembly 14 including the tube assembly 20 extending axially. The tube assembly 20 includes the rotatable inner tube 28 having the lumen 30 disposed coaxially within the outer tube 26. The inner tube 28 forms the inner cutting window 36, and the outer tube 26 forms the outer cutting window 42. The inner and outer cutting windows 36, 42 define the cutting window 22 of the tube assembly 20. The method may also includes the steps of providing the projection 112 within the lumen 30 of the inner tube 28 with at least a portion of the projection 112 disposed within the distal region 34 of the inner tube 28 with the projection 112. In certain embodiments, the projection 112 positioned distal to the proximal boundary 101 of the cutting window 22. The projection 112 provides a reduced cross sectional area to the inner tube 28 relative to a cross sectional area of the lumen proximal to the projection 112. In certain embodiments, the projection 112 is the volume $V_{112}$ that occupies the volume $V_{20}$ of the lumen 30 distal to the proximal boundary 101 of the cutting window 22. The method includes the step of applying the cutting window to a surgical site of a patient and rotating the inner tube 28 relative to the outer tube 26 by the drive assembly 12 to cut the material 106 by an interaction of the inner cutting window 36 and the outer cutting window 42 on the patient, wherein the projection 112 reduces the size of the material 106 removed through the cutting window 22 to reduce clogging of the tube assembly 20.

Figure 20:
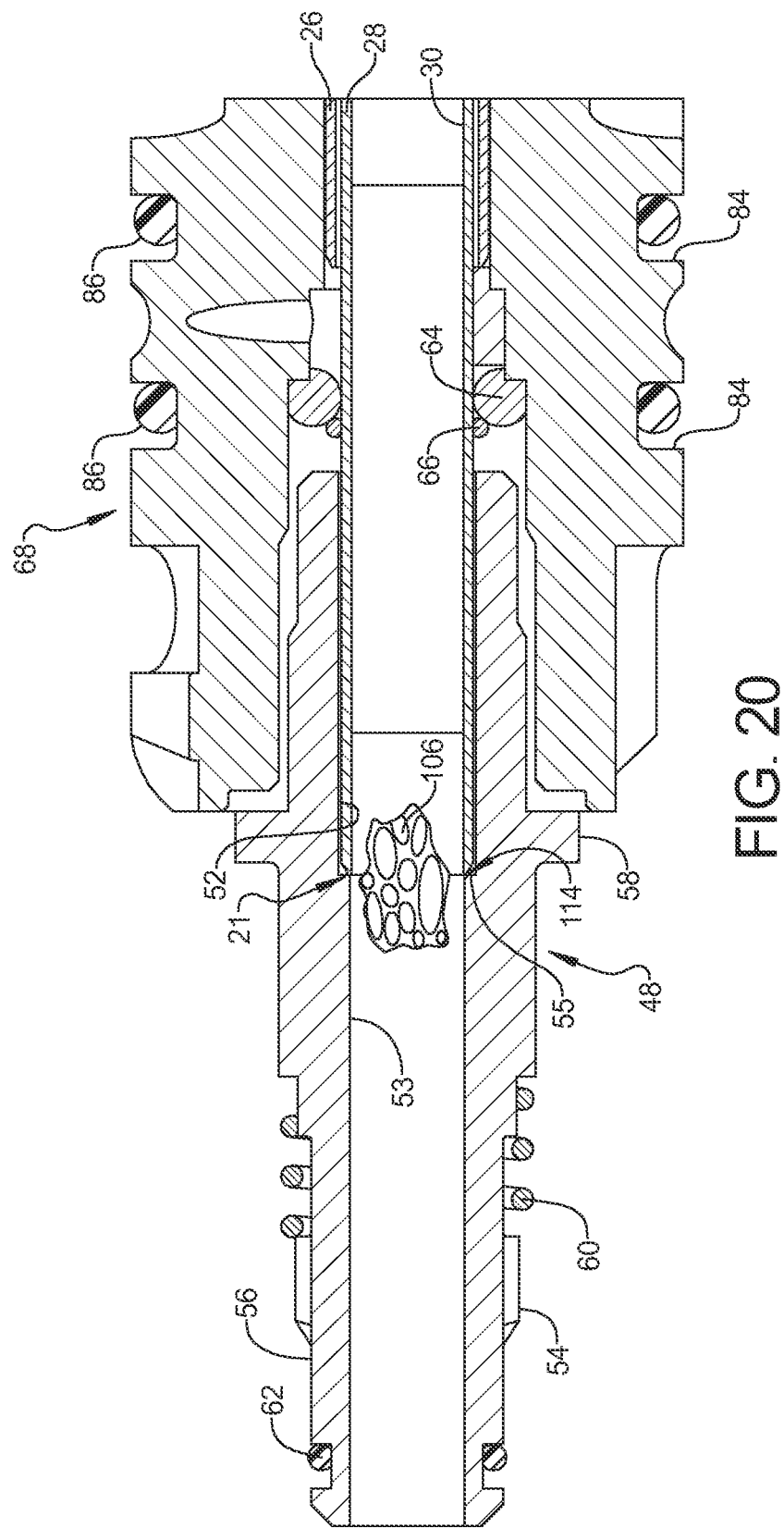
FIG. 20 is a cross-sectional view of the surgical instrument of FIG. 1 taken along lines 20-20.

The surgical instrument 10 of the present disclosure also advantageously reduces the likelihood of clogging at or just proximal to the tube assembly 20 of the surgical instrument 10. FIG. 20 is a cross sectional view of a portion of the surgical instrument of FIG. 1, showing in particular an interface 114 between the tube assembly 20 and the drive hub 48. As mentioned, the hub member 50 of the drive hub 48 includes the reduced diameter portion 56 defining the reduced aperture 53 in communication with the aperture 52 of the drive hub 48 (and the connecting hub 68). The lip 55 is formed by the decrease in diameter from the aperture 52 to the reduced aperture 53. The inner tube 28 has an axial length longer than an axial length of the outer tube 26 such that the inner tube 28 extends past the proximal region 38 of the outer tube 26 and into the connecting hub 68 and the drive hub 48, as shown in FIG. 20.

During assembly of the surgical instrument 10, such as when coupling the tube assembly 20 with the drive hub 48, the inner tube 28 is slidably inserted within the aperture 52 of the drive hub 48 and positioned adjacent or in an abutting relationship with the lip 55. The lip 55 facilitates appropriate axial positioning the tube assembly 20 relative to the housing 15 and other structures of the surgical instrument 10. The lumen 30 of the inner tube 28 is in fluid communication with the reduced aperture 53 of the drive hub 48, as shown in FIG. 20, such that reduced material 106 may pass from the lumen 30 to the suction source.

The diameter of the lumen 30 of the inner tube 28 is less than the diameter of the reduced aperture 53 at the interface 114. In other words, the reduced material 106 moves from a smaller cross sectional area of the lumen 30 to a greater cross sectional area of the reduced aperture 53 as the material 106 passes through the interface 114. In effect, the passage through which the reduced material is moving expands, thereby reducing the likelihood of clogging. If, for a contrasting example, the diameter of the lumen 30 of the inner tube 28 was greater than the diameter of the reduced aperture 53, the reduced material 106 may become lodged on the lip 55 and increase the likelihood of clogging at the interface 114.

Thus, according to one exemplary embodiment of the present disclosure, a cutting assembly for a surgical instrument having a drive assembly, said cutting assembly comprising: a tube assembly comprising a cutting window near a distal end and adapted to be applied to a surgical site of a patient, an outer tube, an inner tube coaxially disposed within and rotatable relative to said outer tube with the drive assembly with said inner tube comprising a lumen; and a drive hub coupled to said inner tube with said drive hub defining an aperture adapted to slidably receive a proximal end of said inner tube, and defining a reduced aperture in communication with said aperture, wherein a diameter of said reduced aperture is less than a diameter of said aperture, wherein a diameter of said inner lumen is less than said diameter of said reduced aperture when said proximal end of said inner tube is slidably received within said aperture to reduce clogging of said surgical instrument as removed material moves from said lumen to said reduced aperture of said drive hub. A lip is formed at an interface between said aperture and said reduced aperture with said proximal end of said inner tube adapted to be positioned adjacent to said lip.

Accordingly, the surgical instrument 10 of the present disclosure reduces the occurrence of the clogging by providing the clog-reducing tip 104 having the projection 112 for reducing a cross sectional area of the lumen 30 distal to the proximal boundary 101 of the cutting window 22 and/or for providing the volume $V_{112}$ within the volume $V_{20}$ of the distal region 34 of the tube assembly 20. The size of the material 106 that may enter the distal region 34 of the inner tube 28 is limited and maintained in a position to be further reduced by the cutting action. Further, only material 106 of sufficiently reduced sized may pass through the "throat" of the tube assembly 20, after which the reduced material 106 encounters the larger cross sectional of the lumen 30 also under the influence of suction. The projection 112 may be the insert secured with the lumen 30 of the inner tube 28, or formed integrally with the same, such as by deforming the distal region 34 of the inner tube 28, providing the borehole eccentric to the longitudinal axis 24 of the tube assembly 20, or suitably milling within the inner tube 28 to define the projection 112. The surgical instrument 10 of the present disclosure cuts and aspirates tissue as per current shaver systems utilizing suction. It should be appreciated that, in another embodiment, the surgical instrument 10 may be used with the surgical tools or be a dedicated tool or instrument.

It will be further appreciated that the terms "include," "includes," and "including" have the same meaning as the terms "comprise." "comprises." and "comprising."

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

Embodiments of the disclosure may be described with reference to the following exemplary clauses:

Clause 1-A cutting assembly for a surgical instrument for cutting tissue, said cutting assembly being configured to be coupled to a drive assembly including a motor having a rotatable drive element enclosed in a housing and said cutting assembly comprising: a rotatable first tube having a lumen, said lumen having a proximal region and a distal region, said first tube forming a first cutting window in said distal region; a second tube disposed over said first tube, said second tube having a proximal region and a distal region, said second tube forming a second cutting window in said distal region; said first tube being rotatable relative to said second tube; said proximal region of said window of said lumen having a cross-sectional area greater than a cross-sectional area of said distal region of said lumen such that tissue cut by an interaction of said first cutting window and said second cutting window is of suitable dimensions to allow passage through said first cutting window and said distal region of said lumen to said proximal region of said lumen to prevent clogging of said distal region of said lumen.

Clause 2-A cutting assembly as set forth in clause 1 wherein said proximal region of said lumen has an interior surface and said distal region of said lumen has an inner surface opposite said first cutting window.

Clause 3-A cutting assembly as set forth in clause 2 wherein said inner surface is displaced radially inward relative to said interior surface.

Clause 4-A cutting assembly as set forth in clause 2 wherein said inner surface extends radially and axially at an angle greater than zero relative to said interior surface.

Clause 5-A cutting assembly as set forth in clause 2 including an insert disposed within said distal region of said lumen opposite said first cutting window and forming said inner surface.

Clause 6-A cutting assembly as set forth in clause 5 wherein said insert is bonded to said first tube.

Clause 7-A cutting assembly as set forth in clause 5 wherein said insert includes said inner surface extending radially and axially at an angle greater than zero relative to said interior surface.

Clause 8-A cutting assembly as set forth in clause 5 wherein said insert has one of a generally arcuate, semi-circular, and rectangular cross-sectional profile.

Clause 9-A cutting assembly as set forth in clause 5 wherein said insert is made of one or more different materials.

Clause 10-A cutting assembly as set forth in clause 2 wherein said inner surface is defined by said inner tube in said distal region of said lumen opposite said first cutting window.

Clause 11-A cutting assembly as set forth in clause 2 wherein said inner surface extends axially from a distal end of said distal region of said lumen to one of less than and at least a proximal end of said first cutting window.

Clause 12-A cutting assembly as set forth in clause 11 wherein said first cutting window has an axial length less than an axial length of one of said inner surface and said second cutting window.

Clause 13-A cutting assembly as set forth in clause 11 wherein an angle of said inner surface to a tube wall of said distal region of said lumen is between approximately 20 degrees and approximately 90 degrees.

Clause 14-A cutting assembly as set forth in clause 11 wherein said inner surface has a radial height greater than a radial height of said interior surface.

Clause 15-A cutting assembly as set forth in clause 1 including a third tube disposed over said second tube.

Clause 16-A cutting assembly as set forth in clause 1 wherein said distal region of said lumen has a profile formed by one of a drawing process and a machined process.

Clause 17-A cutting assembly as set forth in clause 16 wherein said distal region of said lumen has a non-circular cross-section.

Clause 18-A cutting assembly as set forth in clause 1 wherein said first cutting window includes at least one cutting edge.

Clause 19-A cutting assembly as set forth in clause 1 including an aspiration path connected to either one of said first tube and said second tube.

Clause 20-A cutting assembly as set forth in clause 1 wherein a cross-section of said distal region of said lumen and a cross-section of said proximal region of said lumen has a ratio of one of 1:1.5, 1:3, and 1:6.

Clause 21-A cutting assembly as set forth in clause 1 wherein an axial length of said first cutting window relative to a diameter of said distal region of said lumen is such that no dimension of a bone chip that is cut is larger than a diameter of said lumen in said proximal region.

Clause 22-A surgical instrument for use on a patient, said surgical instrument comprising: a cutting assembly including a plurality of tubes extending axially, said tubes comprising at least a rotatable inner tube having a lumen, said lumen having a proximal region and a distal region, said inner tube forming an inner cutting window in said distal region, an outer tube disposed over said inner tube, said outer tube having a proximal region and a distal region, said outer tube forming an outer cutting window in said distal region, said inner tube being rotatable relative to said outer tube; a drive assembly including a motor having a rotatable drive element, a housing for enclosing said motor and being removably coupled to said cutting assembly, a suction connection on said housing for connection to a suction source, and a suction passage extending from said inner window through said inner tube and through said housing to said suction connection; an irrigation connection on said housing for connection to a fluid source; an irrigation passage extending through said housing between said irrigation connection and said cutting assembly and between said inner tube and said outer tube to said cutting window to provide lubrication and flush blood, tissue, and bone; a suction connection on said housing for connection to a suction source; a suction passage extending through said housing between said suction connection and said cutting window of said inner tube; and said proximal region of said lumen having a cross-sectional area greater than a cross-sectional area of said distal region of said lumen such that tissue cut by an interaction of said inner cutting window and said outer cutting window of suitable dimensions to allow passage through said inner cutting window and said distal region of said lumen to said proximal region of said lumen to prevent clogging of said distal region of said lumen.

Clause 23-A method of operating a surgical instrument for use on a patient, said method comprising the steps of: providing a cutting assembly including a plurality of tubes extending axially, the tubes comprising at least a rotatable inner tube having a lumen, the lumen having a proximal region and a distal region, the inner tube forming an inner cutting window in the distal region, an outer tube disposed over the inner tube, the outer tube having a proximal region and a distal region, the outer tube forming an outer cutting window in said distal region, the inner tube being rotatable relative to the outer tube; providing a drive assembly including a motor having a rotatable drive element, a housing for enclosing the motor and being removably coupled to the cutting assembly, a suction connection on the housing for connection to a suction source, and a suction passage extending from the inner window through the inner tube and through the housing to the suction connection; providing the proximal region of the lumen having a cross-sectional area greater than a cross-sectional area of the distal region of the lumen; rotating the inner tube relative to the outer tube by the drive assembly; cutting bone and/or tissue by an interaction of the inner cutting window and the outer cutting window on the patient; and allowing passage of cut bone and/or tissue of suitable dimensions through the inner cutting window and the distal region of the lumen to the proximal region of the lumen to prevent clogging of the distal region of the lumen.

Clause 24-A surgical instrument, cutting assembly, and method as disclosed and described herein, including equivalents not specifically recited herein.

The invention claimed is:

1. A cutting assembly configured to be removably coupled to a drive assembly of a surgical instrument, the cutting assembly comprising:
a connecting hub;
a tube assembly extending distally from the connecting hub and defining a cutting window, wherein the tube assembly comprises an outer tube, and an inner tube coaxially disposed within the outer tube and defining a lumen in communication with the cutting window, wherein the inner tube is configured to be rotatable relative to the outer tube with the drive assembly about a longitudinal axis; and
a projection disposed within the inner tube and comprising a distal first portion positioned distal to a proximal boundary of the cutting window and displaced radially inward relative to an interior surface of the inner tube and configured to reduce clogging of the tube assembly.

2. The cutting assembly of claim 1, wherein the projection further comprises a proximal second portion that is angled relative to the distal first portion.

3. The cutting assembly of claim 2, wherein the proximal second portion is oriented at an angle within a range of approximately 20 degrees to approximately 60 degrees relative to the interior surface of the inner tube.

4. The cutting assembly of claim 2, wherein the distal first portion is oriented substantially parallel to the longitudinal axis of the tube assembly.

5. The cutting assembly of claim 2, wherein the proximal second portion is arcuate to provide a smooth transition to the distal first portion.

6. The cutting assembly of claim 1, wherein the projection is positioned about the longitudinal axis radially opposite the cutting window of the tube assembly.

7. The cutting assembly of claim 1, wherein the projection is positioned about less than one half of a circumference of the lumen.

8. The cutting assembly of claim 1, wherein an angle about the longitudinal axis and extending between opposing sides of the projection is within a range of approximately 70 degrees to approximately 180 degrees.

9. The cutting assembly of claim 1, wherein a distance between the proximal boundary of the cutting window and a nearest point on the projection is less than a diameter of the lumen.

10. The cutting assembly of claim 1, wherein the projection is an insert rigidly coupled to the inner tube.

11. The cutting assembly of claim 1, wherein the projection is formed by the inner tube being deformed radially inwardly towards the longitudinal axis.

12. The cutting assembly of claim 1, wherein the projection is formed by a borehole in communication with the lumen and eccentrically positioned relative to the longitudinal axis.

13. The cutting assembly of claim 1, further comprising a covering tube coaxially disposed over at least a portion of the outer tube, wherein the covering tube is malleable.

14. A cutting assembly configured to be removably coupled to a drive assembly of a surgical instrument, the cutting assembly comprising:
a connecting hub;
a tube assembly extending distally from the connecting hub and defining a cutting window, wherein the tube assembly comprises an outer tube, and an inner tube coaxially disposed within the outer tube and defining a lumen in communication with the cutting window, wherein the inner tube is configured to be rotatable relative to the outer tube with the drive assembly; and
a projection disposed within the inner tube and positioned such that a distance between a proximal boundary of the cutting window and a nearest point on the projection is less than a diameter of the lumen;
wherein a thickness of at least a portion of the projection tapers in a proximal direction.

15. The cutting assembly of claim 14, wherein the projection is positioned about a longitudinal axis radially opposite the cutting window of the tube assembly.

16. A cutting assembly configured to be removably coupled to a drive assembly of a surgical instrument, the cutting assembly comprising:
  a tube assembly defining a cutting window and comprising an outer tube, and an inner tube coaxially disposed within the outer tube and defining a lumen in communication with the cutting window, wherein the inner tube is configured to be rotatable relative to the outer tube with the drive assembly; and
  an insert comprising an outer surface conforming and coupled to an interior surface of the inner tube, wherein the insert forms a projection opposite the cutting window and comprises an inner surface configured to maintain material in position for cutting action to continue until the material is sufficiently reduced to pass between a proximal boundary of the cutting window and the insert.

17. The cutting assembly of claim 16, wherein the insert is bonded to the inner tube.

* * * * *